US012741997B2

(12) United States Patent
Rezaei-Araghi et al.

(10) Patent No.: US 12,741,997 B2
(45) Date of Patent: Sep. 22, 2026

(54) SELECTIVE MCL-1 BINDING PEPTIDES

(71) Applicant: MASSACHUSETTS INSTITUTE OF TECHNOLOGY, Cambridge, MA (US)

(72) Inventors: Raheleh Rezaei-Araghi, Brookline, MA (US); Amy E. Keating, Arlington, MA (US)

(73) Assignee: MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 0 days.

(21) Appl. No.: 18/295,214

(22) Filed: Apr. 3, 2023

(65) Prior Publication Data

US 2024/0092849 A1 Mar. 21, 2024

Related U.S. Application Data

(63) Continuation of application No. 17/102,427, filed on Nov. 23, 2020, now abandoned, which is a continuation of application No. 15/772,226, filed as application No. PCT/US2016/059320 on Oct. 28, 2016, now abandoned.

(60) Provisional application No. 62/248,987, filed on Oct. 30, 2015.

(51) Int. Cl.

| | |
|---|---|
| ***C07K 14/47*** | (2006.01) |
| ***A61K 38/17*** | (2006.01) |
| ***A61P 35/00*** | (2006.01) |
| ***C07K 14/62*** | (2006.01) |
| *A61K 38/00* | (2006.01) |

(52) U.S. Cl.

CPC ...... *C07K 14/4747* (2013.01); *A61K 38/1761* (2013.01); *A61P 35/00* (2018.01); *C07K 14/62* (2013.01); *A61K 38/00* (2013.01)

(58) Field of Classification Search

CPC .......... A61P 35/00; A61P 35/02; A61K 38/00; A61K 38/12; A61K 38/1761; C07K 14/4747; C07K 14/001

See application file for complete search history.

(56) References Cited

U.S. PATENT DOCUMENTS

| | | | | |
|---|---|---|---|---|
| 5,446,090 | A | 8/1995 | Harris | |
| 6,348,558 | B1 | 2/2002 | Harris | |
| 7,723,468 | B2 | 5/2010 | Daffre | |
| 8,889,632 | B2 | 11/2014 | Bernal | |
| 11,142,554 | B2 * | 10/2021 | Rezaei-Araghi | A61K 38/16 |
| 2004/0067503 | A1 | 4/2004 | Tan | |
| 2005/0250680 | A1 | 11/2005 | Walensky | |
| 2006/0073161 | A1 | 4/2006 | Breton | |
| 2008/0027145 | A1 | 1/2008 | Huang | |
| 2008/0199890 | A1 | 8/2008 | Letai | |
| 2009/0092582 | A1 | 4/2009 | Bogin | |
| 2009/0275519 | A1 | 11/2009 | Nash | |
| 2010/0273704 | A1 | 10/2010 | Korsmeyer | |
| 2010/0286057 | A1 | 11/2010 | Walensky | |
| 2012/0172285 | A1 | 7/2012 | Walensky | |
| 2014/0363434 | A1 | 12/2014 | Lasters | |
| 2015/0045310 | A1 | 2/2015 | Link | |
| 2016/0095315 | A1 | 4/2016 | Wei | |
| 2018/0128813 | A1 | 5/2018 | Letai | |
| 2018/0201658 | A1 | 7/2018 | Rezaei-Araghi | |
| 2019/0077840 | A1 | 3/2019 | Rezaei-Araghi | |
| 2019/0185531 | A1 | 6/2019 | Keating | |
| 2020/0262914 | A1 | 8/2020 | Xue | |
| 2021/0363207 | A1 | 11/2021 | Rezaei-Araghi | |

FOREIGN PATENT DOCUMENTS

| | | | |
|---|---|---|---|
| WO | 1997028819 | 8/1997 | |
| WO | 1999014259 | 3/1999 | |
| WO | 1999034833 | 7/1999 | |
| WO | 2006000034 | 1/2006 | |
| WO | 2006135985 | 12/2006 | |
| WO | 2008104000 | 8/2008 | |
| WO | 2008121767 | 10/2008 | |
| WO | WO2009099677 A2 * | 8/2009 | A61K 38/12 |
| WO | 2010060112 | 5/2010 | |
| WO | 2010068684 | 6/2010 | |
| WO | 2010148335 | 12/2010 | |
| WO | 2013116829 | 8/2013 | |
| WO | 2016149613 | 9/2016 | |
| WO | WO2016149613 A2 * | 9/2016 | A61K 38/16 |

OTHER PUBLICATIONS

Foight et al. Designed BH3 Peptides with High Affinity and Specificity for Targeting Mcl-1 in Cells. ACS Chem. Biol. 2014, 9, 1962-1968. (Year: 2014).*

Roosenburg et al. Stabilized 111In-Labeled sCCK8 Analogues for Targeting CCK2-Receptor Positive Tumors: Synthesis and Evaluation. Bioconjugate Chem. 2010, 21, 663-670. (Year: 2010).*

Walensky et al. Activation of Apoptosis in Vivo by a Hydrocarbon-Stapled BH3 Helix. Science 2004;305(5689): 1466-1470. (Year: 2004).*

Chain A, Bcl-2-like protein 11. https://www.ncbi.nlm.nih.gov/protein/6X80_A?report=genbank&log$=protalign&blast_rank= 1&RID=BM672WDN015. downloaded Sep. 4, 2025. (Year: 2025).*

Adams et al., "Measming the sequence-affinity landscape of antibodies with massively pamllel titration cmves," eLife, . 2016. 5, 1-27.

Alford et al., "The Rosetta All-Atom Energy Function for Macromolecular Modeling and Design," Journal of Chemical Theory and Computation, 2017, 13(6), 303 I-3048.

Altscimi et aL "Gapped BLAST and PSI-BLAST: a new generation of protein database search programs," Nucleic Acids Res., 1997, 25: 3389-3402.

(Continued)

*Primary Examiner* — Melissa L Fisher
*Assistant Examiner* — Jia-Hai Lee
(74) *Attorney, Agent, or Firm* — Pabst Patent Group LLP

(57) ABSTRACT

Provided herein are peptides that bind Mcl-1. Also provided are compositions containing these polypeptides and methods of using such peptides in the treatment of cancer that include administering to a subject one of the polypeptides.

10 Claims, 6 Drawing Sheets

Specification includes a Sequence Listing.

(56) References Cited

OTHER PUBLICATIONS

Araghi et al., "Rapid Optimization of Mcl-1 Inhibitors using Stapled Peptide Libraries Including Non-Natural Side Chains," ACS Chern. Biol., Epub, 2016 19, 11 (5): 1 238-44: p. 1239.
Arkadash et al., "Development of High Affinity and High Specificity Inhibitors of Matrix Metalloproteinase 14 through Computational Design and Directed Evolution," Journal of Biological Chemistry, 2017, 292(8), 3481-3495.
Arkin et al., (2014) "Small-Molecule Inhibitors of Protein-Protein Interactions: Progressing toward the Reality," Chemistry & Biology, 2014, 21(9), 1102-1114.
Armstrong et al., "The (1+4) Phe-His Interaction Studied in an Alanine-based a-Helix," Journal of Molecular Biology, Mar. 5, 1993, 230(1), 284.
Bechara et al., "Cell-penetrating peptides: 20 years later, where do we stand?," FEBS Lett., 2013, 587(12):1693-1702.
Bedbrook et al., "Machine learning to design integral membrane channelrhodopsins for efficient eukmyotic expression and plasma membrane localization," PLOS Computational Biology, , 2017, 13(10), 1-21.
Berger et al. "Computationally designed high specificity inhibitors delineate the roles of BCL2 family proteins in cm1cer," eLife, Nov. 2, 2016, 5, 1422-1432.
Bennm1 et al., "The Protein Data Bank." Nucleic Acids Research, 2000, 28(1), 235-242.
Bird et aL "Biophysical determinants for cellular uptake of hydrocarbon-stapled peptide helices," Nature Chemical Biology, 20 1 6, 12( I 0), 845-852.
Bird et al., "Chemical Synthesis of Hydrocarbon-Stapled Peptides for Protein Interaction Research and Therapeutic Targeting," Current Protocols in Chemical Biology, Sep. 1, 2011, 99-117.
Bird et al., "Synthesis and Biophysical Characterization of Stabilized a-Helices of BCL-2 Domains," Methods in Enzymol., 2008, 446:369-386.
Blackwell et al., "Highly Efficient Synthesis of Covalently Cross-Linked Peptide Helices by Ring-Closing Metathesis," Angew Chem. Int Ed. 1998, 37: 3281.
Blackwell et al., "Ring-Closing Metathesis of Oiefil1ic Peptides: Design, Synthesis, and StructuralCharacterization ofMacrocyclic Helical Peptides," J. Org. Chern., , 2007 66 5291-5302.
Boersma et al., "Hydropirile scanning as a complement to alanine scam1ing for exploring and 51. manipulating protein-protein recognition: Application to the Bim BH3 domain," Protein Sci., 2008, 1 7(7), 1232.
Bose et al., "Mel-I as a therapeutic target in acute myelogenous leukemia (Λ_ML)," Leukemia Research Reports, 2013, 2(1), 12-14.
Burke et al., "Discovery of Trycyclic Indoles that Potently Inhibit Mcl-1 using Fragment-Based Methods and Structure-Based Design," J. Med. Chem., 2015, 58(9), 3794.
Burnelle et al., "MCL-1-dependent leukemia cells are more sensitive to chemotherapy than BCL-2-dependent counterparts," J. Cell. Bio 2009, 187 429.
Cang et al., "ABT-199 (venetoclax) and BCL-2 iniribitors in clinical development," Journal of Hematology & Oncology, 2015, 8(1): 1-8.
Chames et aL "Therapeutic antibodies: successes, limitations and hopes for the future," British Journal of Phamiacology. 2009, 157 220-33.
Chao et al., "Isolating and engineering human antibodies using yeast surface display," Nature Protocols, 2006, 1(2), 755-768.
C.hatr-aryamontri et al., "The BioGRID interaction database: 2017 update," Nucleic Acids Research, 2017, 45(D), D369-D379.
Chaudhury et al .. "Py Rosetta: a script-based interface for implementing molecular modeling algoritinns using Rosetta," Bioinforniatics, 2010, 26(5), 689-691.
Chen et al., "Designing specific protein-protein interactions using computation, experimental library screening, or integrated methods," Protein Science, 2012, 21(7), 949-963.
Chen et al., "Stmcture-Based Redesign of the Binding Specificity of Anti-Apoptotic Bcl-xL," Journal of Molecular Biology, 2013, 425(1), 171-185.
Chevalier et al "Massively parallel de novo protein design for targeted therapeutics," NaturePublishing Group; 2017, 550: 74-79.
Chi.Ca et al., "Generation of longer emission wavelength red fluorescent proteins using computmionally designed libralies," Proceedings ofthe National Academy of Sciences, 2010, 07(47),20257-20262.
Choi et al., "Bcl-xL promotes metastasis independent of its anti-apoptotic activity," Nature Communications, 2016, 7, 1-I 3.
Computational Design of Ligand Binding Proteins, 2016, Chapter 14, 15 pages.
Crooks et al., "WebLogo: A Sequence Logo Generator," Genome Research, 2004, 14(6), 1188-1190.
Czabotar et al., "Mutation to Bax beyond the BIB Domain Disrupts interactions with Pro-survival67 Proteins and Promotes Apoptosis," Journal of Biological Chemistry, ,2011, 286(9), 7123-7131.
Davey et al., "Improving the accuracy of protein stability predictions with multistate design using a 68. variety of backbone ensembles." Proteins: Structure, Function, and Bioinfomiatics, 2013, 82(5),771-784.
DeBartolo et al., "Genome-Wide Prediction and Validation of Peptides That Bind Human Prosurvival Bcl-2 Proteins," PLoS Computational Biology , 2014, 10(6), 1-13.
DeBartolo et al., "Predictive Bcl-2 Family Binding Models Rooted in Experiment or Structure, "Journal of Molecular Biology, Sep. 7, 2012, 422(1), 124-144.
Deng et al., "BH3 Profiling Identifies Three Distinct Classes of Apoptotic Blocks to Predict 71. Response to ABT-737 and Conventional Chemotherapeutic Agents," Cancer Cell, , 2007, 12(2), 171.
Devi et al, "Antibodies to poly[(2->8)-a-N-acetylneuraminic acid] and poly[(2->9)a-N-72. acetylneurarninic acid] are elicited by immunization of mice with *Escherichia coli* K92 cortjugates: Potential vaccines for groups Band C meningococci and *E.coli* KI," Proc. Nail. A.cad. Sci. USA, 1991, 88:7175-7179.
Dutta et al., "Determinants ofBH3 Binding Specificity for Mcl-1 versus Bcl-xL," Journal of Molecular Biology, 2010, 398(5), 747-762.
Dutta et al., "Peptide Ligands for Pro-survival Protein Bfl-1 from Computationally Guided Library Screening," ACS Chemical Biology, , 2013, 8(4), 778-788.
Dutta et al., "Potent and Specific Peptide Inhibitors of Human Pro-Survival Protein Bcl-xL," Journal of Molecular Biology, 2015, 427(6), 1241-1253.
Eckert et al., "Characterization ofthe steric defense of the HIV-1 gp41 N-trimer region," Protein Science, Dec. 2008, 17(12), 2091-2100.
Edgar " Search and clustering orders of niagnitude faster than BLAST," Bioinformatics, 2010, 26(19), 2460-2461.
Emsley et al., "Features and development of Coot," Acta Crystallographica Section D Biological 2010, 66(4), 486-501.
Zhou et al., "A general-purpose protein design framework based on mining sequence-structure92. relationships in experimentally-derived protein structures," available 2015.
Zheng et al., "Tertiary Stmctural Propensities Reveal fundamental Sequence/Structure Relationships," Structure, 2015, 23(5), 961-971.
Zheng et aL "Sequence statistics of tertiary structural motifs reflect protein stability," PLOS One, May 26, 2017, 12(5), 1-25.
Zheng et aL "Computational Design of Selective Peptides to Discriminate between Similar 89. Domains in an Oncogenic Pathway," Jmmml of Molecular Biology, 2015, 427(2), 491-510.
Yecies et al., "Acquired resistance to ABT-737 in lymphoma cells that up-regulate MCL-1 and BFLI,"Blood, 2010, 115(]6), 3304-3313.
Xiao et al., "immobilized OBOC combinatorial bead array to facilitate multiplicative screening, "Comb. Chern. Throug_tiput Screen,2013, 16(6), 441.
Wong et al., "Direct visualization of Bol-2 family protein interactions using live cell fluorescent protein redistribution assays," Cell death & disease,, 2012: 3(3): 1-10.

(56) References Cited

OTHER PUBLICATIONS

Williams et aL Efficient Asymmetric Synti-Iesis of N-tert-Butoxycarbonyl Amino Acids Using 4-teit-Butoxycarbonyl-5,6-Diphenylmorpholin-2-ONE:(R)-(NteRt-Butoxycarbonyl)Allyyglycine, 2003, 80:31.
Williams et al., "Asymmetric Symhesis of Monosubsti1.uted and a, a-Substituted-Amino Acids via Diastereoselective Glycine Enolate Alkylations," J. Am. Chem. Soc., 1991, 113: 9276.
Wilen et aL "Tales of Resolving Agents and Optical Resolutions", p. 268, University of Notre Dame Press, 1972.
Wilen et al, "Strategies in Optical Resolutions," Tetrahedron, 1977, 33:2725-2736.
Whitehead et al., "Optimization of affinity, specificity and function of designed influenza inhibitors using deep sequencing," Nature Biotechnology. 2012, 30(6), 543-548.
Wenzel et al, "MCLI is deregulated in subgroups of diffuse large B-cell lymphoma," Leukemia, 2012, 27(6), 1381-1390.
Wang et aL "Alignment of distantly related protein structures: algorithm, bound and implications to homologv modeling," Biointonnatics, Jul. 26, 201 L 27(18), 2537-2545.
Walensky et al., "Hydrocarbon-Stapled Peptides: Principles, Practice, and Progress," Journal of Medicinal Chemistry, , 2014, 57(15), 6275-6288.
Walensky et al, "Activation of Apoptosis in Vivo by a Hydrocarbon-Stapled BH3 Helix," Science, 2004, 305:1466-1470.
Verma et al., "Pareto optimization of combinatorial mutagenesis libraries," TEEEIACM Transactions on Computational Biology and Bioinformatics, Jul. 23, 2018, 1-12.
Vanhee et al., "B1iX: a database of protein building blocks for structural analysis, modeling and design" Nucleic Acids Research, , 2010, 39(suppl I), D435-D442.
UniProt Consortium, "UniProt the universal protein knowledgebase," Nucleic Acids Research, 2016, 45(D 1 ), D1 58-D 169.
Tompa et al., "A Million Peptide Motifs for the Molecular Biologist," Molecular Cell, 2014, 55(2), I 61-169.
Szu et al., "Relation between Structure and immunologic Properties of the Vi Capsular Polysaccharide," IllfecL Immun., 1991, 59:4555-4561.
Szu et al, "Vi Capsular Polysaccharide-Protein Conjugates for Prevention of Typhoid fever," J.Exp. Med., 1987, 166:1510-1524.
Szu et al, "Laboratory and Preliminary Clinical Characterization of Vi Capsular Polysaccharide-Protein Conjugate Vaccines," Infect Immun 1994, 62:4440-4444.
Szu et al, "Comparative Immunogenicities of Vi Polysacchmide-Protein C01liugates Composed of 169. Cholera Toxin or Its B Subunit as a Carrier Bound to High- or Lower-Molecular-Weight Vi, "Infection and Immunity, 1989, 57:3823-3827.
Stewart et al., "The MCL-1 BH3 Helix is an Exclusive MCL-1 inhibitor at1d Apoptosis Sensitizer,"Nat. Chem. Biol., 2010, 6(8), 1-17.
Stebbins et al., "Structure-based design of covalent Sia.h inhibitors," Chem Biol., 20 I 3, 20(8):973-82.
Shirian et al., Converting a broad matrix metallopmteinase family inhibitor into a specific inhibitor of MMP-9 and MMP-14 FEBS Letters, 2018 592(7), 1122-1134.
Shannon & Veerapana, "Covalent protein modification: the current landscape of residue-specific electrophiles," Curr. Opin. Chem. Biol., , 2015, 24, 18-26.
Senft et al., "Selective Induction of Cell Death in Melanoma Cell Lines through Targeting of Mcl-1 and AL" Plus One, , 2012, 7(1), 1-11.
Schymkowitz et al., "The FoldX web server: an online force field," Nucleic Acids Research, 2005, 33 (Web Server), \,V382-W388.
Schwaize et aL "In Vivo Protein Transduction: Delivery of a Biologically Active Protein into the Mouse," Science, 1999, 285(5433), 1569-1572.
Schoenwaelder et al., "Bcl-xL-inhibitory BH3 mimetics can induce a transient thrombocytopathy that undermines the hemostatic function of platelets," Blood, 20 II, I 18(6), 1663-1674.
Schen et al., "Bcl-xL is an oncogenic dliver in colorectal cancer," Cell Death & Disease, 2016, 7(8), e2342-e2342.
Smola et al., "A tutorial on support vector regression," Statistics and computing, Aug. 1, 2004, 4(3): I 99-222.
Sc hafme iste r et al, "An Ail-Hydrocarbon Cross-Linking System for Enhancing the H elicity and Metabolic Stability of Peptides," J. Am. Chem. Soc, 2000, 122:5891-5892.
Salvat et al., "Computationally optimized deimmunization libraries yield highly mutated enzymes 156. with low immunogenicity and enhanced activity," Proceedings of the National Academy of Sciences, 2017, 1-9.
Ryvkin et al, "Phage display peptide libraries: deviations from randomness and correctives," Nucleic Acids Research, 2018, 46(9), e52-e52.
Souers et al., "ABT-199, a potent and selective BCL-2 inhibitor, achieves anti.tumor activity while sparing platelets," Nature Medicine, 2013, I 9(2), 202-208.
Ryan et al., "IBH3: simple, fixable BH3 profiling to detennine apoptotic prirrring in primary tissue by flow cytometr," Biol. Chem., Jul. 1, 2016, 397:671-678.
Ryan et al., "Heightened mitochondiral priming is the basis for apoptotic hypersensitivity of CD4+CD8+ !by mocvtes," Proc. Nall. A.cad. Sci. 2010, 107(29), 1 2895-900.
Ryan et al., "BH3 profiling in whole cells by 11uorimeter or FACS," Methods, 2013, 61(2), 156-164.
Roosenburg et al., "Stabilized 111 In-labeled sCCK8 analogues for targeting CCK2-receptor positive tumors: synthesis and evaluation," Bioconj' :_ I _~~ ate Chem., March | 9, 20 JO, 21(4), 663-670.
Romero et al., "Navigating the protein fitness landscape with Gaussian processes," Proceedings of the National Academy of Sciences, , 2013, 110(3), El 93-E201.
Roelu-1 et aL "A General Framework for Development and Data Analysis of Competitive High-49. Throughput Screens for Small-Molecule Inhibitors of Protein-Protein Interactions by Fluorescence Polarization," Biochemistry, 2004, 43(51), 16056-16066.
Roberts et al., "Computational Design of a PDZ Domain Peptide Inhibitor that Rescues CFTRActivity," PLoS Computational Biology , 2012, 8(4), 1-13.
Rezaei et al., "Iterative optimization y i.elds Mcl-1-tm-geting stapled peptides with selective 147. cytotoxicit-y to Mcl-1-dependent cancer cells," Proceedings of the National Academy of Sciences, 2018, 115(5), E886-E895.
Reich et al., "SORTCERY—A High-Throughput Method to Affinity Rank Peptide Ligands." Journal of Molecular Biology, Jun. 5, 2015, 427( 1), 2135-2150.
Rei.Ch et al "Generating High-Accuracy Peptide-Binding Data in High Throughput with Yeast 145. Surface Display and SORTCERY," Computational Design ofLi.gm1d Binding Proteins, 2016, 233-247.
Qian, et al., "Discovery and Mechanism of Highly Efficient Cyclic Cell-Penetrating Peptides," Biochemistry, 2016, 55(18), 2601-2612.
Procko et aL "A Computationally Designed Inhi.bi.tor of an Epstein-Barr Viral Bcl-2 Protein Induces Apoptosis in Infected Cells," Cell Jun. 19, 2014, 157(7), 1644-1656.
Potapov et al., "Data-Driven Prediction and Design ofbZIP Coiled-Coil Interactions," PLOS Computational Biology, Feb. 19, 2015, 11(2), 1-29.
PCT International Preliminary Report on Patentability in International Appin. No. PCT/US2019/051410, dated Mar. 9, 2021.
PCT international Search Report in International Application No. PCT/US2013/024617, dated Jun. 20, 2013.
PCT International Search Report and Written Opinion mailed Sep. 23, 2016 No. PCT/IfS2016/023118.
PCT International Search Report and Witten Opinion in International Application No. PCT/US2016/059320, dated May 22, 2017.
PCT International Search Report and Written Opinion in International AppIn. No. PCT/US2019/51410, dated Feb. 18, 2020.
PCT international Search Report and Written Opinion in International Appin. No. PCT/US2017/43219, dated Jan. 8, 2018.
Otwinowski el aL "[20] Processing of X-ray diffraction data collected in oscillation mode," Methods Enzvmol, 1997, 276:307-326.

(56) References Cited

OTHER PUBLICATIONS

Opfennan, "Attacking cancer's Achilles heel: antagonism of anti-apoptotic BCL-2 family members," The FEBS Journal , 2015, 283(14), 2661-2675.
Oltersdorf et al., "An inhibitor ofBcl-2 family proteins induces regression of solid tumours," Nature, 2005, 435(7042), 677-681.
Olsson et al., "IJpregulation of bfl-1 is a potential mechanism of chemoresistance in B-cell chroniclymphocytic leukaemia," British Journal of Cancer, ,2007, 97(6), 769-777.
Okamoto et al, "Stabilizing the pro-apoptotic BimBH3 helix (BimSAHB) does not necessarily enhance affinity orbiolo~;ical activity," ACS Chemical Biology, Feb. 15, 2013, 8(2):297-302.
Nischan et al., "Covalent Attachment of Cyclic TAT Peptides to GFP Results in Protein Delivery 130. into Live Cells with Immediate Bioavailability," Angewandte Chemie International Edition, , 2014, 54(6), 1950-1953.
Negron et al., "A Set of Computationally Designed Orthogonal Antiparallel Homodimers that 129 Expands the Synthetic Coiled-Coil Toolldt," Journal of the American Chemical Society, 2014, 136(47), 16544-16556.
Needleman et aL "A general method applicable to the search for similarities in the amino acid sequence of two proteins," Journal of Molecular Biology, Mar. 28, I 970 48(3 ), 443-453.
Mufioz et al., "Development of the multiple sequence approximation within the AGADIR model of 127. a-helix formation: Comparison with Zimm-Bragg and Lifson-Roig formalisms," Biopoly mers, 1997, 41(5), 495-509.
Montero et al., "Why do BCL-2 inhibitors work and where should we use them in the clinic?" Cell Death & Differentiation, 2018, 250 ), 56-64.
Moldoveanu et al., "Many players in BCL~2 family affairs," Trends in Biochemical Sciences, 2014, 39(3), 101-111.
Miles et al., "Hydrocarbon constrained peptides—understanding preorganisation and binding affinity," Chemical Science, 2016, 7(6), 3694-3702.
McCoy et al., "Phaser crystallographic software," Journal of Applied Crystallography, 2007, 40(4):658-674.
McConkey et al., "Discrimination of native protein stmctures using atom-atom contact scoring," Proceedings of the National Academy of Sciences,2003, 100(6), 3215-3220.
Matochko et al., "Prospective identification of parasitic sequences in phage display screens," Nucleic Acids Research, 2013, 42(3), 1784-1798.
Malik et al., "Role of Capsid Structure and Membrane Protein Processing in Determining the Size120, and Copy Number of Peptides Displayed on the Major Coat Protein of filamentous Bacteriophage," Journal of Molecular Biology, 1996, 260(1).
Mackenzie et al., "Tertiary alphabet for the observable protein structural universe," Proceedings of the National Academy of Sciences, 2016, 1 13(47), 7438-7447.
Mackenzie et al., "Protein structural motifs in prediction and design," Current Opinion in Structural Biology, 2017, 44, ]6]-167.
Lewis et al., "Anchored Design of Protein-Protein Interfaces," PLoS One, 2011, 6(6), 1-14.
Lessene et al., "Structure-guided design of a selective BCL-A'L inhibitor," Nature Chemical Biology, 2013, 9(6), 390-397.
Lee et al., "Novel Bcl-2 Homology-3 Domain-like Sequences Identified from Screening 115. Randomized Peptide Libraries for Inhibitors of the Pro-survival Bcl-2 Proteins," Journal of Biological Chemistry 2009, 284(45), 31315-31326.
Lee et al, "Conformational Changes in Bcl-2Pro-survival Proteins Determine Their Capacity to Bind Ligands," J. Biol. Chem, 2009, 284: 30508-30517.
Larkin et al., "Clustal Wand Clustal X version 2.0," Bioinfonnatics 2007, 23(21), 2947-2948.
Kumar et al.,m Novel Polymeric Nanoparticles for Intracellular Delivery of Peptide Cargos; 2014, 74( 12),3271-~3281.
Kuang et al., "DO111\1HNO 2.0: integrating structurally resolved protein-, RNA-, and DNA-mediated macromolecular interactions," Database, 2016, 2016: 1-2.
Kritzer, "Stapled Peptides: Magic bullets in nature's arsenal." Natlire Chemical Biology, 2010, vol. 6, No. 8, 566-567.
Kotschy et al., "The MCLI inhibitor S63845 is tolerable and effective in diverse cancer models," Nature, 2016, 538(7626), 477-482.
Koss et aL "Defining specificity and on-target activity of BH3-mimetics using engineered B-ALL cell lines." Oncotarget, 2016. 7(10):11500-11511.
Kingsford et al., "Solving and analyzing side-chain positioning problems using linear and integer programing," Bioinformatics, 2004, 21(7), 1028-1039.
Kawamoto et aL "Design of Triazole-stapled BCL9 a-Helical Peptides to Target the B-CateniniB-105. cell CLL/lymphoma 9 (BCL9) Protein-Protein Interaction," Journal of Medicinal Chemistry 2012. 55:1137-1146.
Karanicolas et al., "Computational design of affinity and specificity at protein-protein interfaces," Current Opinion in Structural Biology, 2009, 19(4), 458-463.
Kim et al., "Synthesis of all-hydrocarbon stapled a-helical peptides by 1ing-closing olefin metathesis," Nat Protoc.2011, 6(6). 761.
Jenson et aL "Epistatic mutations in PUMA BH3 drive an alternate binding mode lo potently and selectively inhibit anti-apoptotic Bfl-L" Elifo, 2017, 6, I-23.
Jenson et al "Peptide design by optimization on a data-parameterized protein internction landscape," Proceedings of the National Academy of Sciences, 2018, 115( 44):EI0342-EI0351.
Jacobs et al., "SwiftLib: rapid degenerate-codon-library optimization through dynamic programming," Nucleic Acids Research, Dec. 24, 2015, 43(5), e34-e34.
Jacobs et al., "Design of structurally distinct proteins using strategies inspired by evolution," Science, May 6, 2016, 352(6286), 687-690.
Hiraki et aL"Targeting JvITJCI-C suppresses BCL2Al in triple-negative breast cancer," Signal Transduction and Targeted Therapy, 2018.
Hem1,m et al., "Completing the family portrait of the anti-apoptotic Bcl-2 proteins: Crystal stmcture of human Bfl-1 in complex vvith Bim," FEBS Letters, 2008, 582(25-26), 3590-3594.
Henikoff et al., "Amino acid substitution matrices from protein blocks," Proceedings of the National Academy of Sciences, 1992, 89(22), !0915-10919.
Henchey et al., "Contemporary strategies for the stabilization of peptides in the a-helical confomiation," Current Opinion in Chemical Biology, Dec. 1, 2008, I 2(6):692-7.
He et al., "Compositional Bias in Nafve and Chemically-modified Phage-Displayed Libraries uncovered by Paimd-end Deep Sequencing," Scientific Reports, Jan. 19, 2018, 8(1), 1-14.
Grigoryan et al., "Design of protein-interaction specificity gives selective bZIP-binding peptides," Nature, Apr. 2009, 458(7240), 859-864.
Gorelik et al., "Inhibition of SCF ubiquitin ligases by engineered ubiquitin variants that target the 93. Cull binding site on the Skpl-F-box interface," Proceedings of the National Academy of Sciences, 2016, 113(13), 3527-3532.
Gietz et al, "Transfonnation of yeast by lithium acetate/single-stranded carrier DNA/polyethylene glvcol method. Methods Enzymol," 2002, 350:87-96.
Gautier et al .. "HELIQUEST: a web server to screen sequences with specific-helical properties," Bioinfomiatics, 24(18), 210 I-2102.
Gai et al., "Yeast smface display for protein engineering and characterization," Current Opinion in Structural Biology, 2007 17(4), 467-473.
Frappier et al., "PixelDB: Protein-peptide complexes annotated vvith structural conservation of the peptide binding mode," Protein Science 2018. 27(1), 276-285.
Fowler et al., "High-resolution mapping of protein sequence-fonction relationships," Nature Methods 2010, 7(9), 741-746.
Foight et al., "Locating Herpesvims Bcl-2 Homologs in the Specificity Landscape of Anti-Apoptotic Bcl-2 Proteins," Jonrnal of Molecular Biology, 427(15), 2468-2490.
Foight et al., "Designed BH3 Peptides with High Affinity and Specificity for Targeting Mcl-I in Cells," ACS Chemical Biology, 23, 2014, 9(9), I 962-1968.

(56) References Cited

OTHER PUBLICATIONS

Foight et aL "Enriching peptide libraries for binding affinity and specificity through computationally directed library design," Methods Mol Biol., 2014, 1561:213-232.
Fleishman et al., "Computational Design of Proteins Targeting the Conserved Stem Region of Influenza Hemagglutinin," Science, 201 i, 332(6031), 8 I 6-82 I.
Fire et al., "Mcl-1-Bim complexes accommodate surprising point mutations via minor structural dialoges," Protein Science.2010, 19: 507-19.
Fernandez-Fuentes et al., "A supersecondary structure library and search algorithm for modeling loops in protein structures," Nucleic Acids Research, 2006, 34, 2085-2097.
Feng et aL "A topological and conformational stability alphabet for multipass membrane proteins," Nature Chemical Biology, 16, 12(3 ). 167-173.
Fattom et al., "Semm Antibody Response in Adult Volunteers Elicited by I11lection of Streptococus 80. pneumoniae Type 12F Polysaccharide Alone or Conjugated to Diptberia Toxoid," Infect. 1990, 58 2309-2312.
EP European Supplementary Search Report in Applti. No. EP16765822, dated Jul. 24, 2018, 22 pages.

* cited by examiner

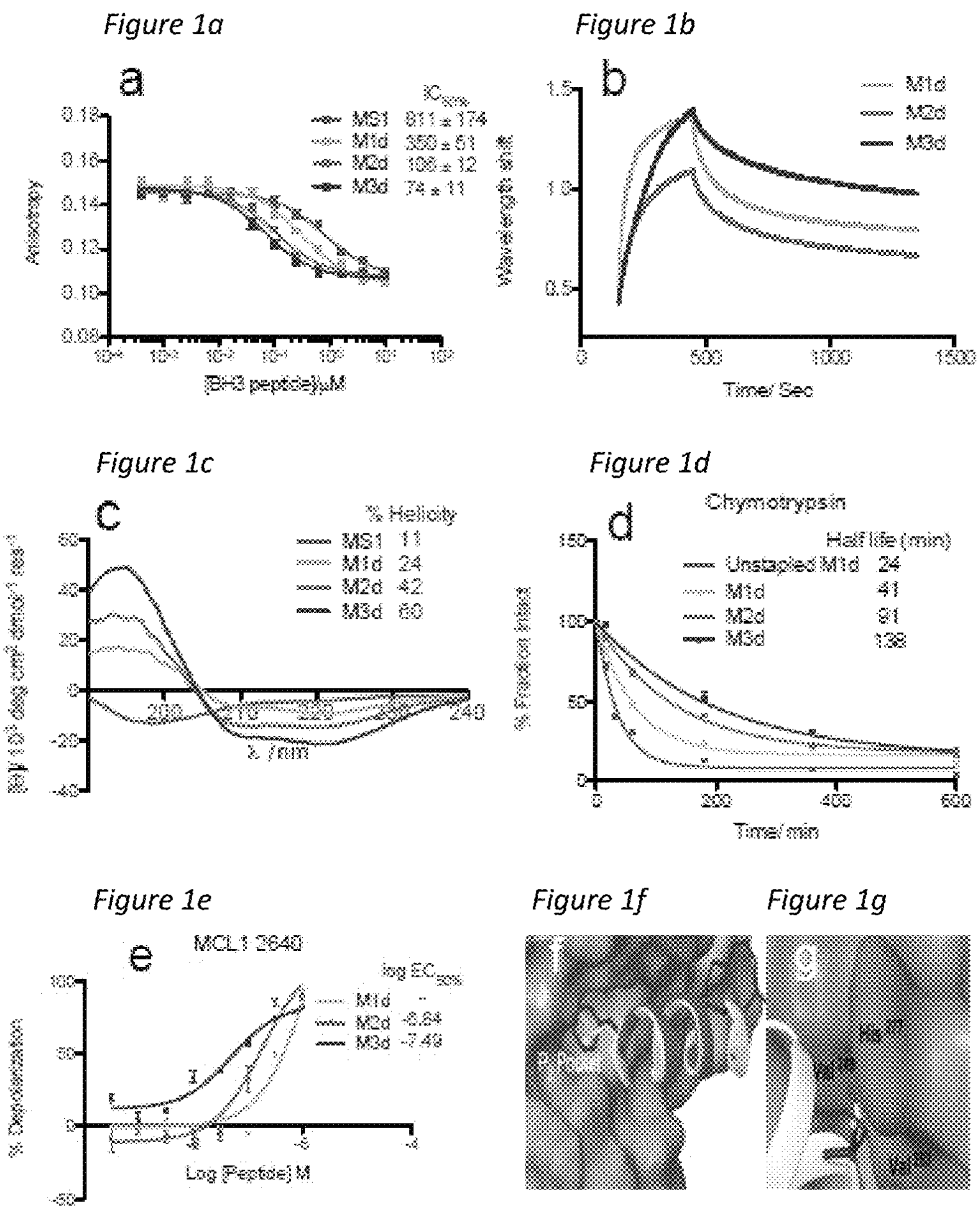
FIG. 1 a-g

Figure 2a
Figure 2b
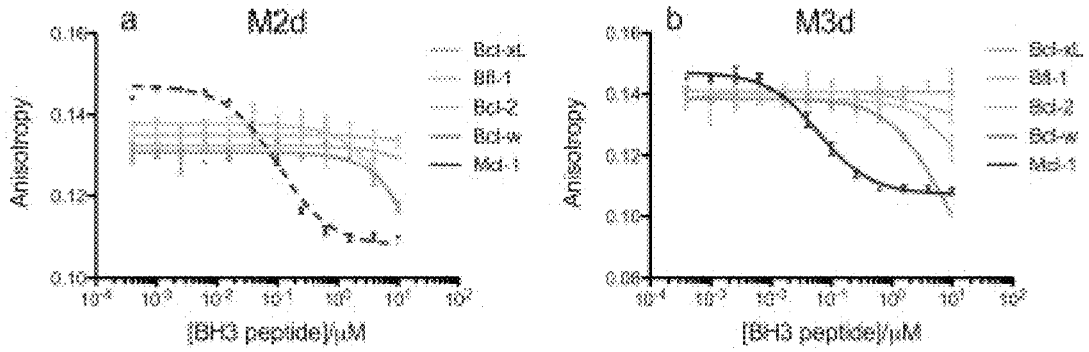
*FIG. 2 a-b*
Figure 3a
Figure 3b
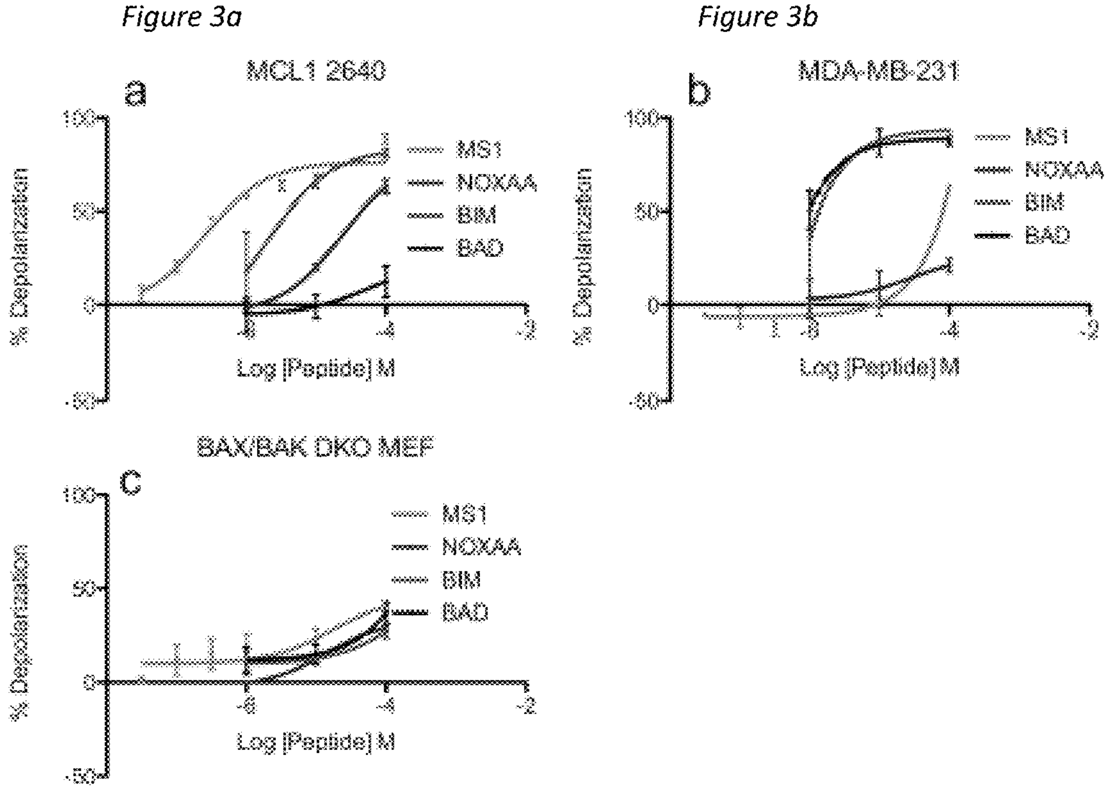
Figure 3c
*FIG. 3 a-c*

*Figure 4a*
*Figure 4b*
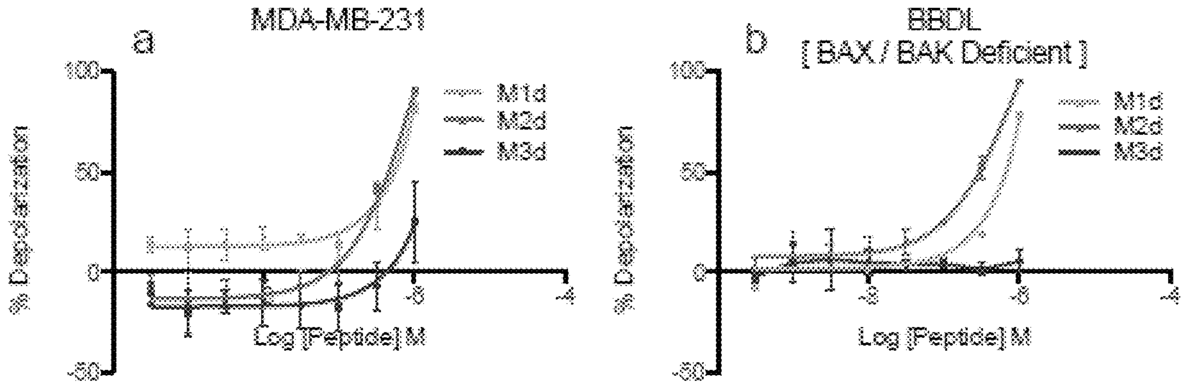
*FIG. 4 a-b*
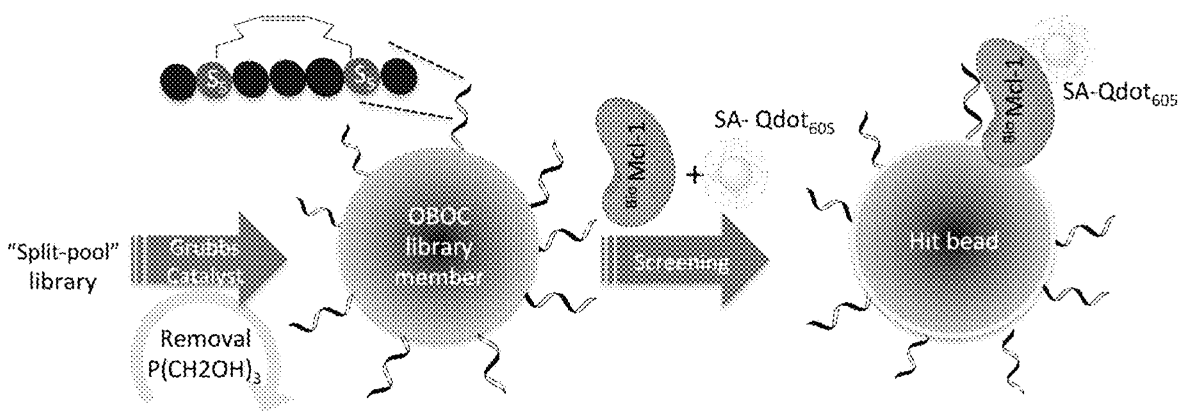
*FIG. 5*

| Peptide templates | Sequence |
|---|---|
| Non-stapled | IWB$X_1$QG$X_2X_3$RLGDEINAYYARR |
| Stapled | IWB$X_1$QG$X_2X_3$RLGDEI$S_5$AYY $S_5$RR |
$S_5$= α-4-pentenyl alanine, J= Aminoisobutyric acid (Aib), Z= Cyclohexyl alanine (Cha), B= Norleucine
$X_1$= Aib, Thr, Val, Ala
$X_2$= Nle, 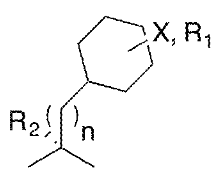 , 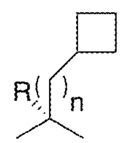 , 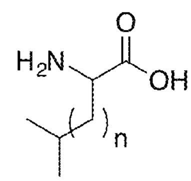
$R_1$ = alkyl
$R_2$ = H, Me
X = halogen
n = 1, 2, 3
R = H, Me
n = 1, 2, 3
n = 1, 2, 3
$X_3$= Arg, Asp, Gln
FIG. 6
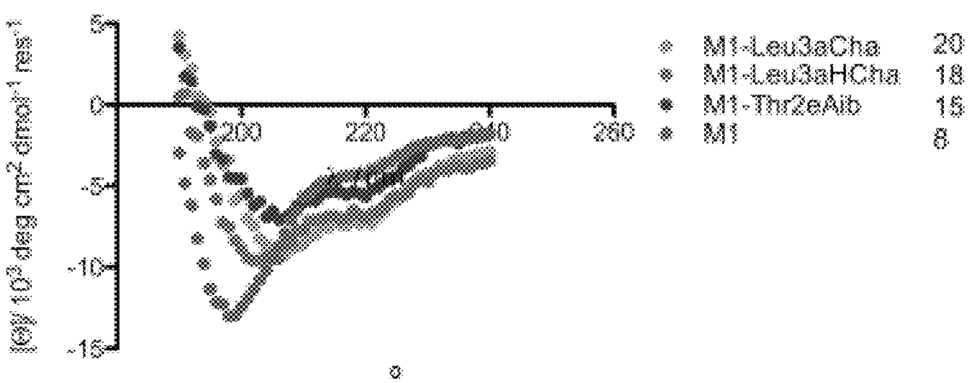
FIG. 7

```
                         SEQUENCE LISTING

Sequence total quantity: 20
SEQ ID NO: 1            moltype =   length =
SEQUENCE: 1
000

SEQ ID NO: 2            moltype = AA  length = 21
FEATURE                 Location/Qualifiers
MOD_RES                 3
                        note = Norleucine
VARIANT                 15
                        note = Any amino acid available for crosslinking
VARIANT                 19
                        note = Any amino acid available for crosslinking
REGION                  1..21
                        note = See specification as filed for detailed description
                         of substitutions and preferred embodiments
source                  1..21
                        mol_type = protein
                        organism = Synthetic construct
SEQUENCE: 2
IWXTQGLRRL GDEIXAYYXR R                                         21

SEQ ID NO: 3            moltype = AA  length = 21
FEATURE                 Location/Qualifiers
MOD_RES                 3
                        note = Norleucine
MOD_RES                 4
                        note = 2-aminoisobutyric acid
VARIANT                 15
                        note = Any amino acid available for crosslinking
VARIANT                 19
                        note = Any amino acid available for crosslinking
REGION                  1..21
                        note = See specification as filed for detailed description
                         of substitutions and preferred embodiments
source                  1..21
                        mol_type = protein
                        organism = Synthetic construct
SEQUENCE: 3
IWXXQGLRRL GDEIXAYYXR R                                         21

SEQ ID NO: 4            moltype = AA  length = 21
FEATURE                 Location/Qualifiers
MOD_RES                 3
                        note = Norleucine
MOD_RES                 4
```

-continued

```
                         note = 2-aminoisobutyric acid
SITE                     7
                         note = Cyclohexylalanine
VARIANT                  15
                         note = Any amino acid available for crosslinking
VARIANT                  19
                         note = Any amino acid available for crosslinking
REGION                   1..21
                         note = See specification as filed for detailed description
                          of substitutions and preferred embodiments
source                   1..21
                         mol_type = protein
                         organism = Synthetic construct
SEQUENCE: 4
IWXXQGXRRL GDEIXAYYXR R                                              21

SEQ ID NO: 5             moltype = AA  length = 21
FEATURE                  Location/Qualifiers
MOD_RES                  3
                         note = Norleucine
MOD_RES                  4
                         note = 2-aminoisobutyric acid
VARIANT                  15
                         note = Any amino acid available for crosslinking
REGION                   1..21
                         note = See specification as filed for detailed description
                          of substitutions and preferred embodiments
source                   1..21
                         mol_type = protein
                         organism = Synthetic construct
VARIANT                  19
                         note = Any amino acid available for crosslinking
SEQUENCE: 5
IWXXQGLQRL GDEIXAYYXR R                                              21

SEQ ID NO: 6             moltype = AA  length = 21
FEATURE                  Location/Qualifiers
MOD_RES                  3
                         note = Norleucine
MOD_RES                  4
                         note = 2-aminoisobutyric acid
VARIANT                  15
                         note = Any amino acid available for crosslinking
MOD_RES                  19
                         note = Any amino acid available for crosslinking
REGION                   1..21
                         note = See specification as filed for detailed description
                          of substitutions and preferred embodiments
source                   1..21
                         mol_type = protein
                         organism = Synthetic construct
SEQUENCE: 6
IWXXQGLDRL GDEIXAYYXR R                                              21

SEQ ID NO: 7             moltype = AA  length = 21
FEATURE                  Location/Qualifiers
MOD_RES                  3
                         note = Norleucine
VARIANT                  19
                         note = Any amino acid available for crosslinking
REGION                   1..21
                         note = See specification as filed for detailed description
                          of substitutions and preferred embodiments
source                   1..21
                         mol_type = protein
                         organism = Synthetic construct
VARIANT                  15
                         note = Any amino acid available for crosslinking
SEQUENCE: 7
IWXTQGLQRL GDEIXAYYXR R                                              21

SEQ ID NO: 8             moltype = AA  length = 21
FEATURE                  Location/Qualifiers
MOD_RES                  3
                         note = Norleucine
SITE                     7
                         note = Cyclohexylalanine
REGION                   1..21
                         note = See specification as filed for detailed description
```

```
                         of substitutions and preferred embodiments
source                  1..21
                        mol_type = protein
                        organism = Synthetic construct
SEQUENCE: 8
IWXTQGXRRL GDEINAYYAR R                                           21

SEQ ID NO: 9            moltype = AA  length = 21
FEATURE                 Location/Qualifiers
MOD_RES                 3
                        note = Norleucine
SITE                    7
                        note = Homo-cyclohexylalanine
REGION                  1..21
                        note = See specification as filed for detailed description
                         of substitutions and preferred embodiments
source                  1..21
                        mol_type = protein
                        organism = Synthetic construct
SEQUENCE: 9
IWXTQGXRRL GDEINAYYAR R                                           21

SEQ ID NO: 10           moltype = AA  length = 21
FEATURE                 Location/Qualifiers
MOD_RES                 3
                        note = Norleucine
MOD_RES                 4
                        note = 2-aminoisobutyric acid
REGION                  1..21
                        note = See specification as filed for detailed description
                         of substitutions and preferred embodiments
source                  1..21
                        mol_type = protein
                        organism = Synthetic construct
SEQUENCE: 10
IWXXQGLRRL GDEINAYYAR R                                           21

SEQ ID NO: 11           moltype = AA  length = 21
FEATURE                 Location/Qualifiers
MOD_RES                 3
                        note = Norleucine
MOD_RES                 4
                        note = 2-aminoisobutyric acid
SITE                    7
                        note = Cyclohexylalanine
REGION                  1..21
                        note = See specification as filed for detailed description
                         of substitutions and preferred embodiments
source                  1..21
                        mol_type = protein
                        organism = Synthetic construct
SEQUENCE: 11
IWXXQGXRRL GDEINAYYAR R                                           21

SEQ ID NO: 12           moltype = AA  length = 21
FEATURE                 Location/Qualifiers
MOD_RES                 3
                        note = Norleucine
MOD_RES                 4
                        note = 2-aminoisobutyric acid
SITE                    7
                        note = Homo-cyclohexylalanine
REGION                  1..21
                        note = See specification as filed for detailed description
                         of substitutions and preferred embodiments
source                  1..21
                        mol_type = protein
                        organism = Synthetic construct
SEQUENCE: 12
IWXXQGXRRL GDEINAYYAR R                                           21

SEQ ID NO: 13           moltype = AA  length = 23
FEATURE                 Location/Qualifiers
source                  1..23
                        mol_type = protein
                        organism = Synthetic construct
SEQUENCE: 13
RPEIWMTQGL RRLGDEINAY YAR                                         23
```

-continued

```
SEQ ID NO: 14           moltype = AA  length = 21
FEATURE                 Location/Qualifiers
MOD_RES                 3
                        note = Norleucine
MOD_RES                 4
                        note = 2-aminoisobutyric acid, Thr, Val or Ala
MOD_RES                 7
                        note = Norleucine, Leu, modified Leu or absent
VARIANT                 8
                        note = Arg, Asp or Gln
source                  1..21
                        mol_type = protein
                        organism = Synthetic construct
SEQUENCE: 14
IWXXQGXXRL GDEINAYYAR R                                            21

SEQ ID NO: 15           moltype = AA  length = 21
FEATURE                 Location/Qualifiers
MOD_RES                 3
                        note = Norleucine
MOD_RES                 4
                        note = 2-aminoisobutyric acid, Thr, Val, or Ala
MOD_RES                 7
                        note = Norleucine, Leu, modified Leu or absent
VARIANT                 8
                        note = Arg, Asp or Gln
MOD_RES                 15
                        note = Alpha-4-pentenyl alanine
MOD_RES                 19
                        note = Alpha-4-pentenyl alanine
source                  1..21
                        mol_type = protein
                        organism = Synthetic construct
SEQUENCE: 15
IWXXQGXXRL GDEIXAYYXR R                                            21

SEQ ID NO: 16           moltype = AA  length = 21
FEATURE                 Location/Qualifiers
MOD_RES                 3
                        note = Norleucine
MOD_RES                 4
                        note = 2-aminoisobutyric acid
SITE                    7
                        note = Cyclohexylalanine
source                  1..21
                        mol_type = protein
                        organism = Synthetic construct
SEQUENCE: 16
IWXXQGXRRL GDEINAYYAR R                                            21

SEQ ID NO: 17           moltype = AA  length = 21
FEATURE                 Location/Qualifiers
MOD_RES                 3
                        note = Norleucine
MOD_RES                 4
                        note = 2-aminoisobutyric acid
SITE                    7
                        note = Homo-cyclohexylalanine
source                  1..21
                        mol_type = protein
                        organism = Synthetic construct
SEQUENCE: 17
IWXXQGXRRL GDEINAYYAR R                                            21

SEQ ID NO: 18           moltype = AA  length = 21
FEATURE                 Location/Qualifiers
MOD_RES                 3
                        note = Norleucine
SITE                    7
                        note = Cyclohexylalanine
source                  1..21
                        mol_type = protein
                        organism = Synthetic construct
SEQUENCE: 18
IWXTQGXRRL GDEINAYYAR R                                            21

SEQ ID NO: 19           moltype = AA  length = 21
FEATURE                 Location/Qualifiers
MOD_RES                 3
```

-continued

```
                         note = Norleucine
SITE                     7
                         note = Homo-cyclohexylalanine
source                   1..21
                         mol_type = protein
                         organism = Synthetic construct
SEQUENCE: 19
IWXTQGXRRL GDEINAYYAR R                                       21

SEQ ID NO: 20            moltype = AA  length = 21
FEATURE                  Location/Qualifiers
MOD_RES                  3
                         note = Norleucine
source                   1..21
                         mol_type = protein
                         organism = Synthetic construct
SEQUENCE: 20
IWXTQGLRRL GDEINAYYAR R                                       21
```

SELECTIVE MCL-1 BINDING PEPTIDES

CROSS-REFERENCE TO RELATED APPLICATIONS

This application is a continuation and claims priority to U.S. Application Ser. No. 17/102,427, filed Nov. 23, 2020, which claims priority to U.S. application Ser. No. 15/772,226, filed Apr. 30, 2018, which is a § 371 National Stage Application PCT/US2016/059320, filed Oct. 28, 2016, which claims the benefit of U.S. Provisional Application Ser. No. 62/248,987, filed on Oct. 30, 2015. The entire contents of the foregoing are incorporated herein by reference.

SEQUENCE LISTING

This application contains a Sequence Listing that has been submitted electronically as an XML file named 39076-0005003_SL_ST26.xml. The XML file, created on Apr. 3, 2023, is 44,143 bytes in size. The material in the XML file is hereby incorporated by reference in its entirety.

TECHNICAL FIELD

This disclosure relates to peptides that bind Mcl-1 and methods of using such peptides in the treatment of cancer.

BACKGROUND

Mcl-1 is one of the most frequently amplified genes in cancers and an important factor in resistance to chemotherapeutic agents. Mcl-1 is a member of a family of anti-apoptotic proteins that have homology to Bcl-2 and contain a so-called BH3 domain. Mcl-1 and others members of the family (e.g., Bcl-xL, Bcl-2, Bcl-w, Bfl-1 and Bcl-b) block apoptosis by interfering with the homo-oligomerizing of Bak and Bax. The anti-apoptotic proteins either bind directly to Bax and Bak or bind related pro-apoptotic activator proteins (Bim, Bid and Puma), preventing activation of Bax and Bak. Other proteins having BH3-domain, called sensitizers, antagonize anti-apoptotic function by binding competitively with Bax/Bak and activators.

Agents that selectively bind Mcl-1 compared to other members of the Bcl-2 family of anti-apoptotic proteins, such as Bcl-xL or Bcl-2, may be useful in treating a variety of cancers.

SUMMARY

The present disclosure describes peptides mimicking BH3 motifs that bind human Mcl-1. The peptides are relatively selective for binding Mcl-1 in that they bind human Mcl-1 with greater affinity than they bind one or more of several proteins considered human homologs of Bcl-1, for example, Bfl-1, Bcl-w, Bcl-xL and Bcl-2.

In some aspects, the present disclosure provides a compound comprising, consisting of, or consisting essentially of the amino acid sequence 1F 1G 2A 2B 2C 2D 2E 2F 2G 3A 3B 3C 3D 3E 3F 3G 4A 4B 4C 4D 4E 4F 4G 5A (SEQ ID NO: 1), wherein 1F is R or a conservative substitution or is missing; 1G is P or a conservative substitution or is missing; 2A is E or a conservative substitution or is missing; 2B is I or a conservative substitution; 2C is W or a conservative substitution; 2D is M or a conservative substitution, or norleucine (B); 2E is T or a conservative substitution, V or a conservative substitution, 2-aminoisobutyric acid (Aib), or X; 2F is Q or a conservative substitution; 2G is G or a conservative substitution; 3A is L or a conservative substitution, F or a conservative substitution, pentafluoro phenylalanine, cyclohexyl alanine (Cha), or homo-cyclohexyl alanine (H-Cha); 3B is R or a conservative substitution, W or a conservative substitution, Q or a conservative substitution, D or a conservative substitution, Y or a conservative substitution, Aib, D-phenyl glycine, α,α methyl leucine, α,α methyl phenylalanine, or X; 3C is R or a conservative substitution; 3D is L or a conservative substitution; 3E is G or a conservative substitution; 3F is D or a conservative substitution; 3G is E or a conservative substitution; 4A is I or a conservative substitution; 4B is N or a conservative substitution, or X; 4C is A or a conservative substitution; 4D is Y or a conservative substitution; 4E is Y or a conservative substitution; 4F is A or a conservative substitution, or X; 4G is R or a conservative substitution or is missing; 5A is R or a conservative or is missing; provided that 2E, 3A, 3B, 4B and 4F are not T, L, R, N and A respectively, wherein X is an amino acid whose side chain is replaced with an intermolecular link to another amino acid. In some cases 1F, 1G and 2A are missing. In some cases, 2D, 4B and 4F are B, N and A respectively.

In some aspects, the present disclosure provides a compound comprising the amino acid sequence 1F 1G 2A 2B 2C 2D 2E 2F 2G 3A 3B 3C 3D 3E 3F 3G 4A 4B 4C 4D 4E 4F 4G 5A (SEQ ID NO: 1), wherein 1F is R or a conservative substitution or is missing; 1G is P or a conservative substitution or is missing; 2A is E or a conservative substitution or is missing; 2B is I or a conservative substitution; 2C is W or a conservative substitution; 2D is M or a conservative substitution, or norleucine (B); 2E is T or a conservative substitution, V or a conservative substitution, 2-aminoisobutyric acid (Aib), or X; 2F is Q or a conservative substitution; 2G is G or a conservative substitution; 3A is L or a conservative substitution, F or a conservative substitution, pentafluoro phenylalanine, cyclohexyl alanine (Cha), or homo-cyclohexyl alanine (H-Cha); 3B is R or a conservative substitution, W or a conservative substitution, Q or a conservative substitution, D or a conservative substitution, Y or a conservative substitution, Aib, D-phenyl glycine, α,α methyl leucine, α,α methyl phenylalanine, or X; 3C is R or a conservative substitution; 3D is L or a conservative substitution; 3E is G or a conservative substitution; 3F is D or a conservative substitution; 3G is E or a conservative substitution; 4A is I or a conservative substitution; 4B is N or a conservative substitution, or X; 4C is A or a conservative substitution; 4D is Y or a conservative substitution; 4E is Y or a conservative substitution; 4F is A or a conservative substitution, or X; 4G is R or a conservative substitution or is missing; 5A is R or a conservative or is missing; provided that 2E, 3A, 3B, 4B and 4F are not T, L, R, N and A respectively, and wherein the side chains of two amino acids separated by 3 or 6 amino acids are optionally replaced by an intramolecular cross-link. In some cases 1F, 1G and 2A are missing. In some cases, 2D, 4B and 4F are B, N and A respectively.

In some cases the compound comprises at least one amino acid that is not one of the common, naturally-occurring amino acids at a position selected from the group consisting of 2E, 3A, and 3B. For example, an amino acid that is not one of the 20 common, naturally-occurring amino acids may be 4-hydroxyproline, α-4-pentenyl alanine, aminoisobutyric acid (Aib), cyclohexyl alanine (Cha), norleucine, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-aminocyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(═O)C6H5; —CF3; —CN; -halo; —NO2; CH3), disubstituted phenylalanines, substituted tyrosines (e.g., further substituted with -Q=O)C6H5; —CF3; —CN; -halo; —NO2; CH3), or statine. Additionally, the amino acids can be derivatized to include amino acid residues that are hydroxylated, phosphorylated, sulfonated, acylated, and glycosylated.

In some embodiments, the compound comprises, consists of, or consists essentially of the amino acid sequence IWBTQGChaRRLGDEINAYYARR (SEQ ID NO: 8), wherein up to 6 (e.g., 1, 2, 3, 4, 5 or 6) of the amino acids are replaced by another amino acid. In some cases, no more than 2 of the amino acids are replaced by another amino acid. In some cases, none of the amino acids are replaced by another amino acid. In some cases the substitution is a conservative substitution. In some cases, neither B nor Cha is substituted.

In some embodiments, the compound comprises, consists of, or consists essentially of the amino acid sequence IWBTQGH-ChaRRLGDEINAYYARR (SEQ ID NO: 9), wherein up to 6 (e.g., 1, 2, 3, 4, 5 or 6) of the amino acids are replaced by another amino acid. In some cases, no more than 2 of the amino acids are replaced by another amino acid. In some cases, none of the amino acids are replaced by another amino acid. In some cases, the substitution is a conservative substitution. In some cases, neither B nor H-Cha is substituted In some embodiments, the compound comprises, consists of, or consists essentially of the amino acid sequence IWBAibQGLRRLGDEINAYYARR (SEQ ID NO: 10), wherein up to 6 (e.g., 1, 2, 3, 4, 5 or 6) of the amino acids are replaced by another amino acid. In some cases, no more than 2 of the amino acids are replaced by another amino acid. In some cases, none of the amino acids are replaced by another amino acid. In some cases, the substitution is a conservative substitution. In some cases, neither B nor Aib is substituted.

In some embodiments, the compound comprises, consists of, or consists essentially of the amino acid sequence IWBAibQGChaRRLGDEINAYYARR (SEQ ID NO: 11), wherein up to 6 (e.g., 1, 2, 3, 4, 5 or 6) of the amino acids are replaced by another amino acid. In some cases, no more than 2 of the amino acids are replaced by another amino acid. In some cases, none of the amino acids are replaced by another amino acid. In some cases, the substitution is a conservative substitution. In some cases, neither B nor Cha is substituted.

In some embodiments, the compound comprises, consists of, or consists essentially of the amino acid sequence IWBAibQGH-ChaRRLGDEINAYYARR (SEQ ID NO: 12), wherein up to 6 (e.g., 1, 2, 3, 4, 5 or 6) of the amino acids are replaced by another amino acid. In some cases, no more than 2 of the amino acids are replaced by another amino acid. In some cases, none of the amino acids are replaced by another amino acid. In some cases, the substitution is a conservative substitution. In some cases, H-Cha is not substituted In some cases, the side chains of two amino acids separated by 3 or 6 amino acids are replaced by an intermolecular crosslink. In some cases, the two amino acids are separated by 3 amino acids. In some cases, the two amino acids are separated by 6 amino acids.

In some cases the intermolecular crosslink is an alkylene or alkenylene group. In some cases, the intermolecular crosslink is an alkylene group. In some cases, the alkylene group is C7, C8, C9, C10, C11, C12 or C13. In some cases, the intermolecular crosslink is an alkenylene group. In some cases, the alkenylene group is C7, C8, C9, C10, C11, C12 or C13.

In some cases, the intermolecular crosslink is a lactam bridge.

In some cases, the side chains of 4B and 4F form an intermolecular crosslink. In some cases, the amino acid at 4B and the amino acid at 4F are α-4-Pentenyl alanine.

In some cases, the compound comprises, consists of, or consists essentially of the sequence IWBTQGLRRLGDEIXAYYXRR (SEQ ID NO: 2), wherein X is an amino acid whose side chain is replaced with an intermolecular link to another amino acid and wherein up to 6 (e.g., 1, 2, 3, 4, 5 or 6) of the amino acids are replaced by another amino acid. In some cases, no more than two of the amino acids are replaced by another amino acid. In some cases, none of the amino acids are replaced by another amino acid. In some cases, the substitution is a conservative substitution. In some cases, B is not substituted In some cases, the compound comprises, consists of, or consists essentially of the sequence IWBAibQGLRRLGDEIXAYYXRR (SEQ ID NO: 3), wherein X is an amino acid whose side chain is replaced with an intermolecular link to another amino acid and wherein up to 6 (e.g., 1, 2, 3, 4, 5 or 6) of the amino acids are replaced by another amino acid. In some cases, no more than two of the amino acids are replaced by another amino acid. In some cases, the substitution is a conservative substitution. In some cases, none of the amino acids are replaced by another amino acid. In some cases, neither B nor Aib is substituted.

In some cases, the compound comprises, consists of, or consists essentially of the sequence IWBAibQGChaRRLGDEIXAYYXRR (SEQ ID NO: 4), wherein X is an amino acid whose side chain is replaced with an intermolecular link to another amino acid and wherein up to 6 (e.g., 1, 2, 3, 4, 5 or 6) of the amino acids are replaced by another amino acid. In some cases, no more than two of the amino acids are replaced by another amino acid. In some cases, none of the amino acids are replaced by another amino acid. In some cases, none B, Aib and Char are substituted.

In some cases, the compound comprises, consists of, or consists essentially of the sequence IWBAibQGLQRLGDEIXAYYXRR (SEQ ID NO: 5), wherein X is an amino acid whose side chain is replaced with an intermolecular link to another amino acid and wherein up to 6 (e.g., 1, 2, 3, 4, 5 or 6) of the amino acids are replaced by another amino acid. In some cases, no more than two of the amino acids are replaced by another amino acid. In some cases, none of the amino acids are replaced by another amino acid. In some cases, the substitution is a conservative substitution. In some cases, neither B nor Aib is substituted.

In some cases, the compound comprises, consists of, or consists essentially of the sequence IWBAibQGLDRLGDEIXAYYXRR (SEQ ID NO: 6), wherein X is an amino acid whose side chain is replaced with an intermolecular link to another amino acid and wherein up to 6 (e.g., 1, 2, 3, 4, 5 or 6) of the amino acids are replaced by another amino acid. In some cases, no more than two of the amino acids are replaced by another amino acid. In some cases, none of the amino acids are replaced by another amino acid. In some cases, the substitution is a conservative substitution. In some cases, neither B nor Aib is substituted.

In some cases, the compound comprises, consists of, or consists essentially of the sequence IWBTQGLQRLG-DEIXAYYXRR (SEQ ID NO: 7), wherein X is an amino acid whose side chain is replaced with an intermolecular link to another amino acid and wherein up to 6 (e.g., 1, 2, 3, 4, 5 or 6) of the amino acids are replaced by another amino acid. In some cases, no more than two of the amino acids are replaced by another amino acid. In some cases, none of the amino acids are replaced by another amino acid. In some cases, the substitution is a conservative substitution. In some cases, B is not substituted.

In some cases of the compounds described herein, X is α-4-Pentenyl alanine.

In some cases of the compounds described herein, at least one amino acid that is not one of the 20 common, naturally-occurring amino acids is selected from the group consisting of: 4-hydroxyproline, α-4-pentenyl alanine, aminoisobutyric acid (Aib), cyclohexyl alanine (Cha), norleucine, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta-substituted phenylalanines, para-substituted phenylalanines, disubstituted phenylalanines, substituted tyrosines and statine.

In some cases of the compounds described herein, the peptide includes of no more than 24 amino acids. In some cases the peptide includes up to 50 amino acids (e.g., 24, 25, 26, 27, 28, 29, 30, 31, 32, 33, 34, 35, 36, 37, 38, 39, 40, 41, 42, 43, 44, 45, 46, 47, 48, 49, 50, etc.). In some cases, the compounds include at least one amino acid that is not one of the 20 common, naturally-occurring amino acids.

In some cases, the compounds described herein also comprise a detectable label. In some cases, the detectable label is linked to the peptide.

In some cases, the compounds described herein also comprise a moiety linked to the peptide. In some cases, the moiety can be a functional peptide, polyethylene glycol (PEG), alkyl groups (e.g., C1-C20 straight or branched alkyl groups), fatty acid radicals, and combinations thereof. In some cases, the peptide is linked to PEG.

In some cases of the compounds described herein, the peptide is linked to a second peptide or functional moiety. In some cases the second peptide or functional moiety modulates the activity of the compound. For example, in some cases the second peptide or functional moiety modulates the solubility of the compound, modulates the stability of the compound, modulates the ability of the compound to permeabilize a cell, acts to target the compound within/to the cell, labels the compound, modulates the affinity of the compound for MCL-1 and/or other members of the family (e.g., Bcl-xL, Bcl-2, Bcl-w, Bfl-1 and Bcl-b), modulates the specificity of the compound for MCL-1 and/or other members of the family (e.g., Bcl-xL, Bcl-2, Bcl-w, Bfl-1 and Bcl-b), and/or any combination thereof. Modulating the activity of the compounds described herein can be increasing or decreasing the activity.

In some cases of the compounds described herein, the peptides are modified. In some cases, the modification is selected from the group consisting of acetylation, amidation, biotinylation, cinnamoylation, farnesylation, fluoresceination, formylation, myristoylation, palmitoylation, phosphorylation, stearoylation, succinylation, sulfurylation, and combinations thereof.

In some cases of the compounds described herein, the peptides include at least one peptide bond that is replaced by a non-natural peptide bond. In some cases, the peptide bond is replaced by a bond selected from the group consisting of a retro-inverso bonds (C(O)—NH); a reduced amide bond (NH—CH2); a thiomethylene bond (S—CH2 or CH2-S); an oxomethylene bond (O—CH2 or CH2-O); an ethylene bond (CH2-CH2); a thioamide bond (C(S)—NH); a trans-olefin bond (CH═CH); a fluoro substituted trans-olefin bond (CF═CH); a ketomethylene bond (C(O)—CHR) or CHR—C(O) wherein R is H or CH3; and a fluoro-ketomethylene bond (C(O)—CFR or CFR—C(O) wherein R is H or F or CH3.

In some cases, the compounds described herein also comprise a carrier protein.

In some aspects, the present disclosure provides a pharmaceutical composition comprising the compounds described herein. In some aspects, the present disclosure provides a method of treating cancer comprising administering the compound described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIG. 1 *a-g*|Results of circular dichroism, competition assays, BH3 profiling, and stability assays.

FIG. 2 *a-b*|Results of competition fluorescence anisotropy binding experiments.

FIG. 3 *a-c*|Results of BH3 profiling assay of engineered MS1 and native BH3 peptides.

FIG. 4 *a-b*|Results of BH3 profiling assay of stapled BH3 peptides.

FIG. 5|Schematic of one bead one compound library formation.

FIG. 6|Sequences of the Mcl-1 binding peptides and structures of uncommon amino acids.

FIG. 7|Results of circular dichroism to determine helicity.

DETAILED DESCRIPTION

Figure 8:
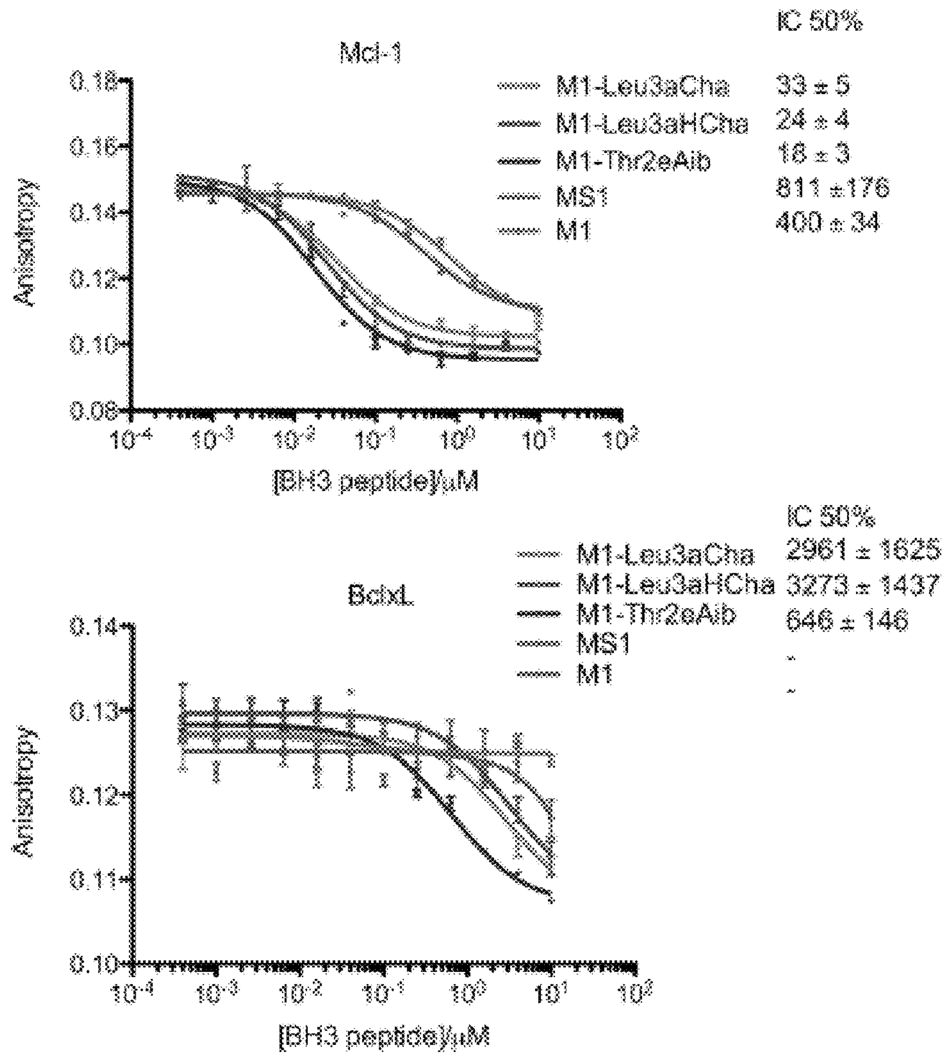
FIG. 8|Results of competition assays to determine binding affinity and specificity.

The present disclosure provides Mcl-1-binding peptides. In some cases, the peptides include amino acids other than the 20 common, naturally-occurring amino acids. In some cases the peptides have an internal (intramolecular) cross-link (or staple) that replaces the side chains of two amino acids that are separated by 3 or 6 amino acids. In some cases the peptides have more than one internal cross-link (e.g., the peptides include two staples or a stitch).

Amino acids are the building blocks of the peptides herein. The term "amino acid" refers to a molecule containing both an amino group and a carboxyl group as well as a side chain. Amino acids suitable for inclusion in the peptides disclosed herein include, without limitation, natural alpha-amino acids such as D- and L-isomers of the 20 common naturally-occurring alpha-amino acids found in peptides (e.g., Ala (A), Arg (R), Asn (N), Cys (C), Asp (D), Gln (Q), Glu (E), Gly (G), His (H), Ile (I), leu (L), Lys (K), Met (M), Phe (F), Pro (P), Ser (S), Thr (T), Trp (W), Tyr (Y), and Val (V), uncommon alpha-amino acids (including, but not limited to α,α-disubstituted and N-alkylated amino acids), common naturally-occurring beta-amino acids (e.g., beta-alanine), and uncommon beta-amino acids. Amino acids used in the construction of peptides of the present invention can be prepared by organic synthesis, or obtained by other routes, such as, for example, degradation of or isolation from a natural source.

There are many known amino acids beyond the 20 common naturally-occurring amino acids, any of which may be included in the peptides of the present invention. Some examples of uncommon amino acids are 4-hydroxyproline, α-4-pentenyl alanine, aminoisobutyric acid (Aib), cyclohexyl alanine (Cha), norleucine, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/para-substituted phenylalanines (e.g., substituted with —C(═O)$C_6H_5$; —$CF_3$; —CN; -halo; —$NO_2$; $CH_3$), disubstituted phenylalanines, substituted tyrosines (e.g., further substituted with -Q=O)$C_6H_5$; —$CF_3$; —CN; -halo; —$NO_2$; $CH_3$), and statine. Additionally, amino acids can be derivatized to include amino acid residues that are hydroxylated, phosphorylated, sulfonated, acylated, and glycosylated, to name a few.

Useful amino acids include:

(F5)

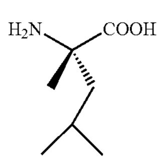

a,a methyl Leu

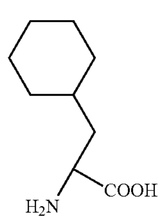

Cha

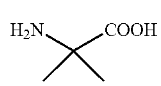

Amino isobutric acid

-continued

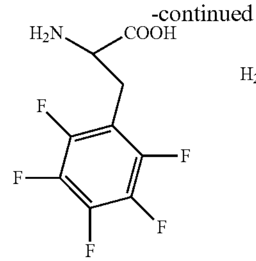

Phe

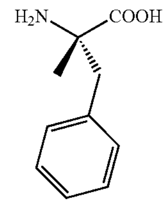

a,a methyl Leu

In some instances, peptides include only common, naturally-occurring amino acids, although uncommon amino acids (i.e., compounds that do not commonly occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc.

In some instances, peptides can include (e.g., comprise, consist essentially of, or consist of) at least seven (e.g., 7, 8, 9, 10, 11, 12, 13, 14, 15, 16, 17, 18, 19, 20, 21, 22) contiguous amino acids of any of SEQ ID NOs: 1-12. In some instances, the peptides can comprise the amino acid sequence of any of SEQ ID NOs: 1-12 with 1, 2, 3, 4, 5 or 6 single amino acid substitutions, e.g., conservative substitutions. In some instances, the peptides can comprise the amino acid sequence of any of SEQ ID NOs: 1-12 and have the side chains of 2 amino acids separated by 3 or 6 amino acids substituted by an internal cross-link and, in addition to the cross-link, include 1, 2, 3, 4, 5 or 6 single amino acid substitutions, e.g., conservative substitutions. In some instances, the peptides can comprise the amino acid sequence of any of SEQ ID NOs: 1-12 and have the side chains of more than 2 amino acids separated by 3 or 6 amino acids substituted by an internal cross-link and, in addition to the cross-link, include 1, 2, 3, 4, 5 or 6 single amino acid substitutions, e.g., conservative substitutions.

In some instances, a "conservative amino acid substitution" can include substitutions in which one amino acid residue is replaced with another naturally-occurring amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

As disclosed above, peptides herein include at least two modified amino acids that together can form an internal (intramolecular) cross-link (or staple), wherein the at least two modified amino acids are separated by: (A) three amino acid (i.e., i, i+4) or (B) six amino acids (i.e., i, i+7). In the case of a cross-between i and i+4 the cross-link can be a C8 alkylene or alkenylene. In the case of a cross-link between i and i+7 the cross-link can be a C11, C12 or C13 alkylene or alkenylene. When the cross-link is an alkenylene there can one or more double bonds. In the case of a cross-link between i and i+4 the cross-link can be a C8 alkyl or alkene. In the case of a cross-link between i and i+7 the cross-link can be a C11, C12 or C13 alkyl or alkene (e.g., a C11 alkene having a single double bond). When the cross-link is an alkene there can be one or more double bonds.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., *J. Org. Chem.,* 66: 5291-5302, 2001; Angew et al., *Chem. Int. Ed.* 37:3281, 1994). As used herein, the term "peptide stapling," includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008121767 and in WO 2010/068684, which are both hereby incorporated by reference. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g., 1, 4 triazole or 1, 5 triazole) crosslinks can be used (Kawamoto et al. 2012 *Journal of Medicinal Chemistry* 55:1137; WO 2010/060112).

Stapling of a peptide using all-hydrocarbon cross-link has been shown to help maintain its native conformation and/or secondary structure, particularly under physiologically relevant conditions (Schafmiester et al., *J. Am. Chem. Soc.,* 122:5891-5892, 2000; Walensky et al., Science, 305:1466-1470, 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncrosslinked (e.g., "unstitched" or "unstapled") peptide.

Peptides herein may include at least two internally cross-linked or stapled amino acids, wherein the at least two amino acids are separated by three (i.e., i, i+4) or six (i.e., i, i+7) amino acids. While at least two amino acids are required to support an internal cross-link (e.g., a staple), additional pairs of internally cross-linked amino acids can be included in a peptide, e.g., to support additional internal cross-links (e.g., staples). For example peptides can include 1, 2 or 3 staples.

Alternatively or in addition, peptides can include three internally cross-linked or stitched amino acids, e.g., yielding two staples arising from a common origin. A peptide stitch includes at least three internally cross-linked amino acids, wherein the middle of the three amino acids forms an internal cross-link (between alpha carbons) with each of the two flanking (not immediately adjacent) modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 3 or 6 amino acids. The number of amino acids on either side of the core (e.g., between the core amino acid and an amino acid cross-linked to the core) can be the same or different.

As noted above an internal tether or cross-link can extend across the length of one helical turn (i.e., about 3.4 amino acids (i.e., i, i+4) or two helical turns (i.e., about 7 amino acids (i.e., i, i+7). Accordingly, amino acids positioned at i and i+4; or i and i+7 are candidates for chemical modification and cross-linking. Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . , cross-links between $Xaa_1$ and $Xaa_5$, or between $Xaa_1$ and $Xaa_8$ are useful as are cross-links between $Xaa_2$ and $Xaa_6$, or between $Xaa_2$ and $Xaa_9$, etc.

As disclosed above, peptides herein may include at least one amino acid that is not one of the 20 common, naturally-occurring amino acids, wherein every position not in that group is a common, naturally-occurring amino acid. In the case of at least one amino acid that is not one of the 20 common, naturally-occurring amino acids, the peptide may not have an internal cross-link (or staple). These uncommon amino acids may help maintain the native conformation and/or secondary structure, particularly under physiologically relevant conditions.

In some instances, peptides can include (e.g., comprise, consist essentially of, or consist of) at least one amino acid, that is not one of the 20 common, naturally-occurring amino acids, in the at least seven (e.g., 7, 8, 9, 10, 11, 12, 13, 14, 15, 16, 17, 18, 19, 20, 21, 22) contiguous amino acids of any of SEQ ID Nos: 1-12.

Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, N Y, 1962); Wilen, S. H. Tables of Resolving Agents and Optical Resolutions p. 268 (EX. Eliel, Ed., Univ. of Notre Dame Press, Notre Dame, IN 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

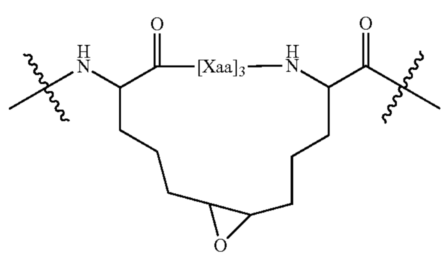

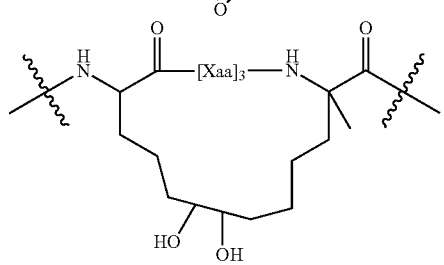

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., an anti-cancer agent such as rapamycin, vinblastine, taxol, etc.). Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a common, naturally-occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using common, naturally-occurring amino acids rather than using a tether that is made by coupling two uncommon amino acids. It is also possible to use a single uncommon amino acid together with a common, naturally-occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

$XO—(CH_2CH_2O)_n—CH_2CH_2—Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched.

Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 common, naturally-occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as $—NH(CH_2)_nC(O)—$, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The stapled and non-stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

In some embodiments, the peptides disclosed herein have an enhanced ability to penetrate cell membranes.

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH 2 protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond ($NH—CH_2$); a thiomethylene bond ($S—CH_2$ or $CH_2—S$); an oxomethylene bond ($O—CH_2$ or $CH_2—O$); an ethylene bond ($CH_2—CH_2$); a thioamide bond (C(S)—NH); a trans-olefin bond (CH═CH); a fluoro substituted trans-olefin bond (CF═CH); a ketomethylene bond (C(O)—CHR) or CHRC (O) wherein R is H or $CH_3$; and a fluoro-ketomethylene bond (C(O)—CFR or CFR—C(O) wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

α, α-Disubstituted amino acids containing olefinic side chains of varying length can be synthesized by known methods (Williams et al. J. Am. Chem. Soc., 113:9276, 1991; Schafmeister et al., J. Am. Chem Soc., 122:5891, 2000; and Bird et al., Methods Enzymol., 446:369, 2008; Bird et al, Current Protocols in Chemical Biology, 2011). For peptides where an i linked to i+7 staple is used (two turns of the helix stabilized) either one S5 amino acid and one R8 is used or one S8 amino acid and one R5 amino acid is used. R8 is synthesized using the same route, except that the starting chiral auxillary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-$S_5$—OH, Fmoc-$R_8$—OH, Fmoc-$R_8$—OH, Fmoc-$S_8$—OH and Fmoc-$R_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, CA). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

In some instances, peptides can include a detectable label. As used herein, a "label" refers to a moiety that has at least one element, isotope, or functional group incorporated into the moiety which enables detection of the peptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to, $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; labels that include immune or immunoreactive moieties, which may be antibodies or antigens, which may be bound to enzymes {e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101}mRh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99}mTc$, $^{14}C$, $^{13}N$, $^{15}O$, $^{32}P$, $^{33}P$ and $^{18}F$.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally-occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafmeister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some embodiments, the peptides are substantially free of contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Pharmaceutical Compositions

One or more of the peptides disclosed herein (e.g., one or more of SEQ ID NOs: 1-12) can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions). In some instances, pharmaceutical compositions can include an effective amount of one or more peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of cancer).

Pharmaceutical compositions of this invention can include one or more peptides and any pharmaceutically acceptable carrier and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-I-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as I-, ϑ-, and K-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the peptides or pharmaceutical compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561, 1991; Szu et al., J. Exp. Med. 166:1510-

1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

Methods of Treatment

The disclosure includes methods of using the peptides herein for the prophylaxis and/or treatment of cancer. The terms "treat" or "treating," as used herein, refers to partially or completely alleviating, inhibiting, ameliorating, and/or relieving the disease or condition from which the subject is suffering.

In general, methods include selecting a subject and administering to the subject an effective amount (a therapeutically effective amount) of one or more of the peptides herein, e.g., in or as a pharmaceutical composition, and optionally repeating administration as required for the prophylaxis or treatment of a cancer.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

EXAMPLES

Described below are studies characterizing variants of MS-1, a previously described peptide that binds Mcl-1 with increased specificity and affinity relative to Bfl-1, Bcl-xL, Bcl-2, and Bcl-w (Foight et al. *ACS Chem. Biol.* 2014, 9, 1962-1968). The variants were characterized for secondary structure, specificity for binding to Mcl-1, affinity of binding to Mcl-1, peptide stability, and functionality in cells. Further, a library was created as a tool to discover novel BH3-like peptides.

Example 1: Characterization of Stapled Variants of MS1

To improve the binding and helicity of MS1 while minimizing its molecular weight, we truncated the peptide and generated a stapled variant by replacing Asn at 4b and Ala at 4f with amino acids containing olefin tethers and performing ruthenium-catalyzed olefin metathesis to yield M1d (see Table 1 for sequences and position notation). Introduction of the hydrocarbon staple at this position of the BH3 domain, which we call site "d" in keeping with prior work, has been shown to promote binding to Mcl-1 (Stewart, M. L.; Fire, E.; Keating, A. E.; Walensky, L. D. *Nat Chem Biol* 2010, 6 (8), 595). The crystal structure of a peptide stapled at position d shows direct hydrophobic contacts made between the staple atoms and the edge of the Mcl-1 binding groove.

The secondary structure and binding of M1d were evaluated in solution using fluorescence polarization assays and circular dichroism (FIGS. 1*a* and *c*). M1d is ~3-fold more helical in solution than MS1. The hydrocarbon stapling strategy also improved Mcl-1-binding affinity and increased peptide resistance to proteolysis, in comparison to MS1 (FIGS. 1*a* and *d*). Although M1d is able to compete effectively with a peptide corresponding to the BH3 region of Bim, which is a native partner for Mcl-1, structural modeling suggested that M1d may not be maximally exploiting the available binding opportunities at three helix positions: 2e, 3a and 3b. Furthermore, modifying a peptide by introducing a staple changes its properties, such that re-optimization of the sequence may be beneficial. However, the virtually unlimited sequence variations that could be studied present a challenge. To date, hydrocarbon stapled peptides have typically been rationally optimized by iterative mutagenesis. Obtaining tight-binding and biologically active molecules often requires many rounds of laborious synthesis and stapling of different peptidic candidates.

The binding curves from representative experiments are shown in FIG. 1. Competition assay of stapled peptides with fluorescently labeled 21mer Bim-BH3 was performed to measure the binding to Mcl-1 (see FIG. 1 (*a*)). The standard errors reported are over three experiments. FIG. 1 (*b*) shows the kinetic analysis of M1d, M2d and M3d binding to Mcl-1, using biolayer interferometry. FIG. 1 (*c*) shows the circular dichroism analysis of unmodified and stapled variants, in 20 mM tris buffer, pH 7.4. HPLC was used to measure the half-lives of unstapled and stapled peptides exposed to chymotrypsin and the half-lives are shown in FIG. 1 (*d*). BH3 profiling of stapled peptides M1d, M2d, and M3d in Mcl-1 2640 cells are shown in FIG. 1 (*e*). Structural overlay of structures of Mcl-1 bound to SAHBd (yellow, PDB 3MK8) and M3d (magenta, model based on 3MK8) can be seen in FIG. 1 (*f*) and the overlaid structures of MS1 (yellow, model based on 3MK8) and M3d (magenta, also a model based on 3MK8) comparing position 2e is seen in FIG. 1 (*g*).

TABLE 1

| Mcl-1 binding peptide | 1F | 1G | 2A | 2B | 2C | 2D | 2E | 2F | 2G | 3A | 3B | 3C | 3D | 3E | 3F | 3G | 4A | 4B | 4C | 4D | 4E | 4F | 4G | 5A |
|---|---|---|---|---|---|---|---|---|---|---|---|---|---|---|---|---|---|---|---|---|---|---|---|---|
| MS1 | R | P | E | I | W | M | T | Q | G | L | R | R | L | G | D | E | I | N | A | Y | Y | A | R | |
| M1d SEQ ID NO: 2 | — | — | — | I | W | B | X | Q | G | L | X | R | L | G | D | E | I | N | A | Y | Y | A | R | R |
| M2d SEQ ID NO: 3 | — | — | — | I | W | B | Aib | Q | G | L | R | R | L | G | D | E | I | X | A | Y | Y | X | R | R |
| M3d SEQ ID NO: 4 | — | — | — | I | W | B | Aib | Q | G | Cha | R | R | L | G | D | E | I | X | A | Y | Y | X | R | R |
| M4d SEQ ID NO: 5 | — | — | — | I | W | B | Aib | Q | G | L | Q | R | L | G | D | E | I | X | A | Y | Y | X | R | R |
| M5d SEQ ID NO: 6 | — | — | — | I | W | B | Aib | Q | G | L | D | R | L | G | D | E | I | X | A | Y | Y | X | R | R |
| M6d SEQ ID NO: 7 | — | — | — | I | W | B | T | Q | G | L | Q | R | L | G | D | E | I | X | A | Y | Y | X | R | R |
| M1 | — | — | — | I | W | B | T | Q | G | L | R | R | L | G | D | E | I | N | A | Y | Y | A | R | R |
| Ma-Leu3aCha SEQ ID NO: 8 | — | — | — | I | W | B | T | Q | G | Cha | R | R | L | G | D | E | I | N | A | Y | Y | A | R | R |
| Ma-Leu3aHCha SEQ ID NO: 9 | — | — | — | I | W | B | T | Q | G | H-Cha | R | R | L | G | D | E | I | N | A | Y | Y | A | R | R |

TABLE 1-continued

| Mcl-1 binding peptide | 1F | 1G | 2A | 2B | 2C | 2D | 2E | 2F | 2G | 3A | 3B | 3C | 3D | 3E | 3F | 3G | 4A | 4B | 4C | 4D | 4E | 4F | 4G | 5A |
|---|---|---|---|---|---|---|---|---|---|---|---|---|---|---|---|---|---|---|---|---|---|---|---|---|
| M1-Thr2eAib SEQ ID NO: 10 | — | — | — | I | W | B | Aib | Q | G | L | R | R | L | G | D | E | I | N | A | Y | Y | A | R | R |
| M1-Leu3aCha/Thr2eAib SEQ ID NO: 11 | — | — | — | I | W | B | Aib | Q | G | Cha | R | R | L | G | D | E | I | N | A | Y | Y | A | R | R |
| M1-Leu3aHCha/Thr2eAib SEQ ID NO: 12 | — | — | — | I | W | B | Aib | Q | G | H-Cha | R | R | L | G | D | E | I | N | A | Y | Y | A | R | R |

Table 1.
X = an amino acid whose side chain is replaced with an intermolecular link to another amino acid (e.g., α-4-pentenyl alanine), B = Norleucine, Aib = Aminoisobutyric acid, Cha = cyclohexyl alanine, and H-Cha = homo cyclohexyl alanine.

Example 2: Identification of Novel Variants Using One Bead One Compound Libraries To accelerate the discovery of therapeutic peptides, we extended the application of one-bead-one-compound libraries (Xiao, W.; Bononi, F. C.; Townsend, J.; Li, Y.; Liu, R.; Lam, K. S. *Comb. Chem. High Throughput Screen.* 2013, 16 (6), 441) by applying on-bead ring—closing metathesis (RCM) to make libraries of BH3-like stapled peptides (FIG. 5). Installation of a staple into a peptide requires incorporation of two appropriately spaced α-methyl-α-alkenyl residues, with defined stereochemical configuration and alkene chain length, followed by RCM on the resin (Kim, Y. W.; Grossman, T. N.; Verdine, G. L. *Nat. Protoc.* 2011, 6 (6), 761). To evaluate conditions that would produce a high-quality stapled peptide library suitable for analysis without purification, and to establish an efficient on-bead screening procedure, we synthesized a first-generation stapled library based on the sequence of Bim BH3 (library LA).

This library incorporated a number of mutations that have been studied previously to serve as controls. The library was synthesized on Tentagel macrobeads and screened for binding to Mcl-1 and Bcl-$x_L$. Bcl-$x_L$ is a paralog of Mcl-1 and an undesired interaction target for candidate inhibitors. The screen entailed bead blocking, incubation with biotinylated Mcl-1 ('Mcl-1), washing, incubation with streptavidin-coated quantum dots (Qdots-SA605), and visualization using a fluorescence microscope. 173 hit peptides, which were selected manually under the microscope, were cleaved from the beads and identified using mass spectrometry. Both the stapling chemistry and subsequent tests for binding were carried out with peptides bound to resin, with one unique peptide per bead. Selected hit peptides were confirmed to bind to Mcl-1 in solution.

Example 3: Optimization of One Bead One Compound Library

To apply this method to the optimization of M1d, a library of 108 stapled peptides (library LB) was designed to be enriched in Mcl-1 binders. Positions 2e, 3a and 3b were diversified with 3, 4 and 9 amino ac-ids, respectively, varying the residue size, hydrophobicity and/or charge (Table 1). Many of the side chains were chosen to be hydrophobic to favor hydrophobic contacts with Mcl-1. We also introduced known helix-inducing side chains to improve the helical content of stapled peptides, which is expected to be poor at the peptide N-terminus because of two Gly residues in the MS1 template. To choose residues for the mutation sites, we used the large amount of mutational data from SPOT arrays and side-chain scanning of BH3 peptides (Dutta, S.; Gullá, S.; Chen, T. S.; Fire, E.; Grant, R. A.; Keating, A. E. *J. Mol. Biol.* 2010, 398 (5), 747; Foight, G. W.; Ryan, J. A.; Gullá, S. V; Letai, A.; Keating, A. E. *ACS Chem. Biol.* 2014, 9 (9), 1962; Boersma, M. D.; Sadowsky, J. D.; Tomita, Y. A.; Gellman, S. H. *Protein Sci.* 2008, 17 (7), 1232). We also analyzed structures of Mcl-1 bound to different BH3 variants using Bioluminate (version 1.9, Schrödinger, LLC, New York, NY, 2015) to select side chains for the library. We incorporated functionalities, beyond those found in the 20 common, naturally-occurring amino acids, that we predicted could access crevices in Mcl-1 that are too distant to be reached by the sidechains found in the 20 common, naturally-occurring amino acids. LB was sorted for binding to Mcl-1 in two rounds of competition screening in which beads were selected that could bind to Mcl-1 in the presence of 12.5- or 50-fold higher concentration of Bcl-xL.

Example 4: Screening of Optimized Library

LB was initially screened under conditions optimized for the first generation library, LA: 0.2 μM $^{Bio}$Mcl-1 in presence of 2.5 μM myc-tagged Bcl-xL ($^{myc}$Bcl-xL). However, for LB we used a Complex Object Parametric Analyzer and Sorter (COPAS) for cell sorting that permits fluorescence-based sorting of up to 300 beads/s. The 5% of beads with highest fluorescence intensities were sorted into 96-well plates. Beads were washed and then post-screened using more stringent conditions: 0.05 μM $^{Bio}$Mcl-1 plus 2.5 μM $^{myc}$Bcl-xl. After incubation with streptavidin-coated quantum dots, beads were further washed and visualized using a fluorescence microscope. 170 brightest beads from a pool of ~10,000 were isolated manually. MALDI mass spectrometry confirmed that the selected beads included at least 6 different sequences out of the possible 108 stapled BH3 peptides. Sequences M1d (32 beads), M2d (48 beads), and M3d (38 beads) were chosen for further analysis (Table 1). Interestingly, M2d and M3d incorporate previously untested side chains at positions 2e and 3a, which are highly conserved in known BH3 motifs.

Example 5: Characterization of M2d and M3d Peptide Binding to Mcl-1

M2d and M3d were tested in solution in competition with a fluorescently labeled Bim BH3 peptide for binding to five human Bcl-2 paralogs (FIG. 1 and FIG. 2). Unlabeled peptides were mixed with fluoresceinated Bim BH3 and one of Mcl-1, Bfl-1, Bcl-w, Bcl-$x_L$, or Bcl-2. The competition experiments indicated that M2d and M3d are both highly selective for Mcl-1 over 4 other anti-apoptotic members and are both considerably tighter binders of Mcl-1 than is M1d. These peptides competed with fluoresceinated Bim 21mer for Mcl-1 binding with half-maximal inhibitory concentrations ($IC_{50}$ values) of 106±12 nM and 72±11 nM, for M2d and M3d respectively (compare with 350 nM for M1d and 811 nM for MS1). Position 2e is usually conserved as small (alanine, glycine, serine) in natural BH3 sequences.

However, previous studies have shown that Mcl-1 can bind BH3 peptides with bulkier threonine and leucine at this site (Foight, G, W.; Ryan, J. A.; Gulla, S. V; Letai, A.; Keating, A. E. *ACS Chem. Biol.* 2014, 9(9), 1962 and Stewart, M. L.; Fire, E.; Keating, A. E.; Walensky, L. D. *Nat Chem Biol* 2010, 6 (8), 595). Our results show that, likewise, introducing the larger, branched 2-aminoisobutyric acid (Aib) at the 2e position in M2d is not only well tolerated but increases binding affinity for Mcl-1. Computational modeling of Aib at 2e in Mcl-1 complexes (2PQK and 3MK8) shows how two methyl groups can be accommodated in the Mcl-1 interface (FIG. 1(*g*)). Interestingly, the largest increase in potency was observed for M3d, which includes Aib at 2e and Cha at 3a. The selection of Cha at 3a was not easily anticipated from the inspection of Mcl-1 complexed with BH3 peptides, and the stabilizing effect was somewhat surprising given that leucine is highly conserved at this position in native BH3 domains. Molecular modeling using Bioluminate predicts that the flexible cyclohexyl moiety of M3d penetrates deep into the previously defined P2 binding pocket of Mcl-1 (FIG. 1(*f*)), explaining the increase in potency of M3d for Mcl-1 over other Bcl-2 paralogs (FIG. 1(*a*))(Burke, J. P.; Bian, Z.; Shaw, S.; Zhao, B.; Goodwin, C. M.; Belmar, J.; Browning, C. F.; Vigil, D.; Friberg, A.; Camper, D. V; Rossanese, O. W.; Lee, T.; Olejniczak, E. T.; Fesik, S. W. *J. Med. Chem.* 2015, 58 (9), 3794). Discovery of unpredictable chemical moieties strongly improving Mcl-1 binding clearly demonstrate the effectiveness of our combinatorial approach.

We used biolayer interferometry to measure the kinetics of binding of stapled peptides to Mcl-1 (FIG. 1(*b*)). We generated biotinylated stapled peptides and attached these to a streptavidin-modified probe surface. Binding of M2d and M3d to Mcl-1 was slower compared to binding of M1d, likely due to rearrangements required for packing of the bulky side chains of Aib and Cha. However, consistent with their higher affinity, dissociation of M2d and M3d from Mcl-1 was even slower compared to M1d. Peptide M3d had the lowest $k_{diss}$ ($1.8\times10^{-4}$) and $K_d$ (5 nM) values.

Example 6: Structural Characterization of M1d, M2d and M3d Peptides

The secondary structure of selected stapled peptides was assessed by circular dichroism (CD) spectroscopy (FIG. 1(*c*)). Interestingly, the observed trend for binding affinities was paralleled by the measured helicity. M2d and M3d showed significantly higher helicity than M1d, with mean residue ellipticity (MRE) at 222 nm of 15,450 and 21,000 deg $cm^2$ $dmol^{-}1$, respectively. Therefore, the increases in helicity can be attributed to both helix-inducing substitutions: Aib at 2e and Cha at 3a (Armstrong, K. M.; Fairman, R.; Baldwin, R. L. *J. Mol Biol.* 1993, 230 (1), 284. and Venkatraman, J.; Shankaramma, S. C.; Balaram, P. *Chem. Rev.* 2001, 101 (10), 3131).

Example 7: Characterization of M1d, M2d and M3d Peptide Stability

All of the stapled MS1 variants that we tested were more protease resistant than un-metathesized M1d, which is a key pharmacologic advantage of the stapling approach. Unstapled M1d has a half-life 2-6-fold shorter than the corresponding stapled peptides (FIG. 1(*d*)). Notably, the protease resistance analysis revealed longer half-lives for both M2d and M3d compared to M1d, indicating the utility of introducing helix-promoting amino acids into a stapled peptide for maximizing protease resistance.

Example 8: BH3 Profiling of Peptide Variants

We performed BH3 profiling to test the function of stapled variants of MS1 in cells. A whole-cell BH3 profiling experiment quantifies the dependence of cancer cell mitochondrial integrity on specific anti-apoptotic proteins and can be predictive of cellular responses to chemotherapy (Ryan, J. A.; Brunelle, J. K.; Letai, A. *Proc. Natl. Acad. Sci.* 2010, 107 (29), 12895 and Ryan, J. A; Letai, A. *Methods* 2013, 61(2), 156). In this assay, permeabilized cells are stained with dye JC1 to monitor mitochondrial membrane integrity in response to increasing doses of BH3 peptides. We used this assay to test the specificity of our Mcl-1-binding stapled peptides in cell lines with different established dependencies on Bcl-$x_L$ and Mcl-1. Mcl-1/Myc 2640 is an engineered murine leukemia cell line overexpressing murine Mcl-1 and Myc, and MDA-MB 231 is a human breast cancer cell line with a primed Bcl-xL-dependent pro-file (Brunelle, J. K.; Ryan, J.; Yecies, D.; Opferman, J. T.; Letai, A. J. *Cell Biol.* 2009, 187 (3), 429 and Ryan, J. A.; Brunelle, J. K.; Letai, A. *Proc. Natl. Acad. Sci.* 2010, 107 (29), 12895). By BH3 profiling using native BH3 peptides from BAD and NOXAA, we confirmed cell line dependencies on these anti-apoptotic proteins (FIG. 3). FIG. 3 shows the BH3 profiling of cell lines using engineered (MS1) and native BH3 peptides (Bim, NoxA). Mcl-1 2640 cell line is dependent on Mcl-1 whereas MDA-MB-231 is dependent on Bcl-$x_L$, as indicated by response to NoxA and Bad, respectively. BBDL is Bax/Bak deficient leukocyte (error bars indicate the standard deviation over 3 or more replicates). Both M1d and M2d showed Bax/Bak independent activity in Bax/Bak deficient cells, indicating non-specific toxicity (FIG. 4). However, peptide M3d showed no activity in Bax/Bak negative cells, consistent with an on-target mechanism, (Deng, J.; Carlson, N.; Takeyama, K.; Dal Cin, P.; Shipp, M.; Letai, A. *Cancer Cell* 2015, 12 (2), 171) and was remarkably potent when tested on Mcl-1/Myc 2640, with an EC 50 value of 30 nM (FIGS. 1(*e*) and 4(*b*). The specificity of M3d was confirmed by the much higher $EC_{50}$ (estimated as >5 mM) observed for the Bcl-$x_L$ dependent cell line MDA-MB 231 (FIG. 4(*a*)).

Example 9: Characterization of Novel Non-Stapled Peptides with Amino Acids that are not the 20 Common, Naturally-Occurring Amino Acids We identified two substitutions that—both in the presence or absence of a staple modification—improve binding to Mcl-1 and preserve a high degree of specificity. These modifications are: replacement of a leucine residue at position "3a" with either cyclohexyl phenylalanine or homo-cyclohexyl phenylalanine and replacement of a threonine at position "2e" with 2-amino isobutyric acid (see Table 1). Both are non-conservative mutations, and the leucine that is substituted in our peptides is highly conserved in natural peptides that bind to Mcl-1, making it somewhat surprising that a change to the larger cyclohexyl phenylalanine or homo-cyclohexyl phenylalanine groups is beneficial. FIG. 6 shows the sequences of both stapled and non-stapled peptides, along with the structures of various uncommon amino acid examples. FIGS. 7 and 8, along with the following describe the binding and biophysical characterization of the new staple-less peptides.

The secondary structure of selected non-stapled peptides with uncommon amino acids was assessed by circular dichroism (CD) spectroscopy at 22° C. in $H_2O$ (FIG. 7). Single point mutations were compared with their parent construct (M1). Increase in helical content can be attributed to the addition of helix-inducing amino acids.

The binding affinity and specificity for the non-stapled peptides with uncommon amino acids were assessed using a competition assay. $IC_{50}$ values for binding to Mcl-1 (target) or Bcl-xL (undesired competitor) were obtained from competition assays with fluoresceinated Bim peptide (FIG. 8). All single point mutations incorporated conferred higher binding affinity to Mcl-1 and preserve selectivity over other Bcl-2 family proteins. Data are the mean and s.d. for at least duplicate experiments.

Example 10: BH3 Profiling of Novel Non-Stapled Peptides

We measured the depolarization of the mitochondrial membrane of p185+ B-ALL cell lines dependent on Mcl-1, Bcl-xL, Bcl-2 or Bfl-1 in response to treatment with unstapled peptides in comparison with MS1. The results for the peptides compared to MS1 at 10 nM are shown in the top panel of FIG. 9. The results of known BH3 peptides at a higher concentration (1011M) are shown in the bottom panel of FIG. 9. In the sequences listed, 1=Aib, 2-aminoisobutyric acid; 2=Cha, cyclohexylalanine; and 3=h-Cha, homo-cyclohexylalanine.

Figure 9:
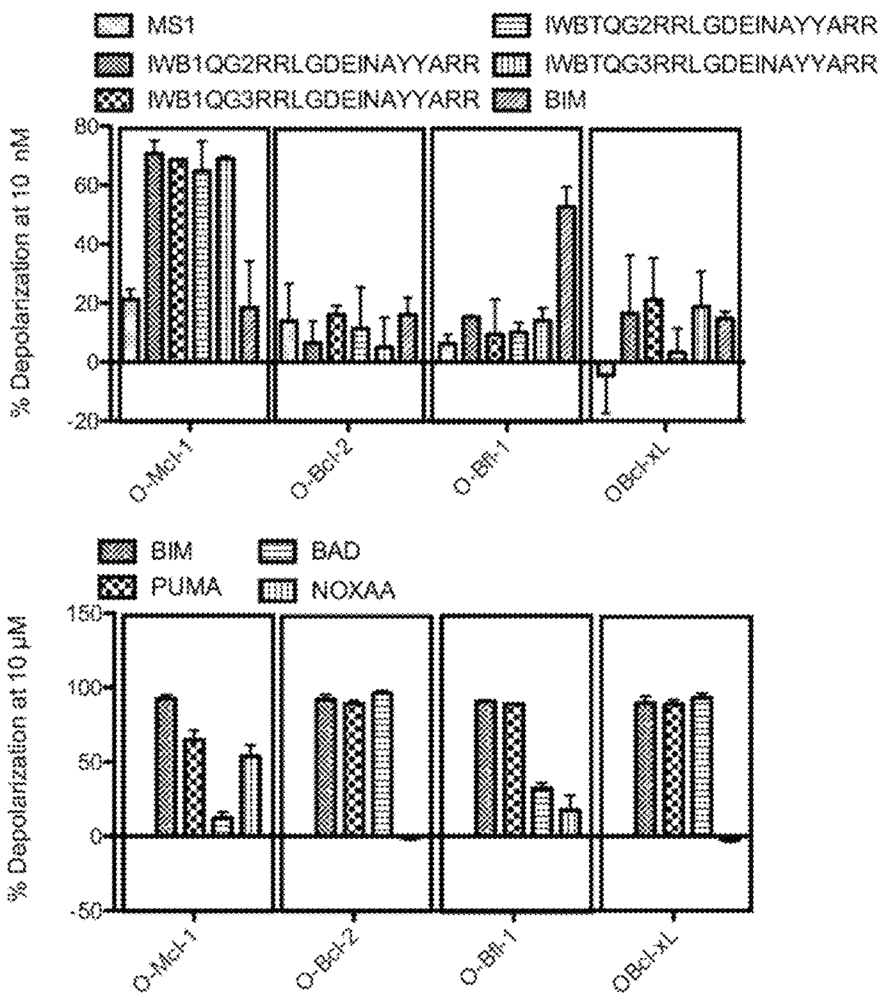
FIG. 9|Results of BH3 profiling assay of peptides with cell lines dependent on Mcl-1, Bcl-xL, Bcl-2, or Bfl-1 (1:Aib, 2-aminoisobutyric acid; 2: Cha, cyclohexylalanine; and 3: hCha, homo-cyclohexylalanine).

The unstapled peptides in the top panel of FIG. 9 were highly potent and selective for inducing MOMP in Mcl-1 dependent, but not Bcl-xL, Bcl-2 or Bfl-1 dependent permeabilized cells at 10 nM. The known peptides (BIM, PUMA, BAD, NOXAA) were less potent and were tested at 10 µM, as shown in the bottom panel of FIG. 9; these peptides were less selective. The over-expressing cell lines are described in: Koss et al. "Defining specificity and on-target activity of BH3-mimetics using engineered B-ALL cell lines." *Oncotarget* (2016) vol. 7 (10) pp. 11500-11, which is incorporated herein in its entirety.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound comprising the amino acid sequence selected from the group consisting of:

(SEQ ID NO: 8) IWBTQGChaRRLGDEINAYYARR, (SEQ ID NO: 9) IWBTQGH-ChaRRLGDEINAYYARR, (SEQ ID NO: 11) IWBAibQGChaRRLGDEINAYYARR, and (SEQ ID NO: 12) IWBAibQGH-ChaRRLGDEINAYYARR;

wherein B is norleucine and H-Cha is homo-cyclohexylalanine.

2. The compound of claim 1, wherein the peptide is 24 amino acids in length.

3. The compound of claim 1, wherein the compound further comprises a moiety linked to a terminal of the peptide, and wherein the moiety is selected from the group consisting of a functional peptide, polyethylene glycol (PEG), alkyl groups, fatty acid radicals, and combinations thereof.

4. The compound of claim 1, wherein the peptide is linked to PEG.

5. A pharmaceutical composition comprising a compound of claim 1.

6. The compound of claim 1, wherein the compound is further modified with a modification selected from the group consisting of acetylation, amidation, biotinylation, cinnamoylation, farnesylation, fluoresceination, formylation, myristoylation, palmitoylation, phosphorylation, stearoylation, succinylation, sulfurylation, and combinations thereof.

7. The compound of claim 1, wherein the compound further comprises a carrier protein.

8. A compound comprising the amino acid sequence IWBAibQGChaRRLGDEINAYYARR (SEQ ID NO: 11), wherein B is norleucine.

9. A compound comprising:

(a) the amino acid sequence: IWBTQGH-ChaRRLGDEINAYYARR (SEQ ID NO: 9) or a variant thereof, wherein B is norleucine and H-Cha is homo-cyclohexylalanine, and wherein the variant comprises up to 3 amino acids substitutions selected from: B is substituted with M, L, I or V; T is substituted with A or V; and R at position 8 of SEQ ID NO: 9 is substituted with Q, D, Aib or Me-Leu;

(b) the amino acid sequence: IWBTQGChaRRLGDEINAYYARR (SEQ ID NO: 8) or a variant thereof, wherein B is norleucine, and wherein the variant comprises up to 3 amino acids substitutions selected from: B is substituted with M, L, I or V; Tis substituted with A or V; and R at position 8 of SEQ ID NO: 8 is substituted with Q, D, Aib or Me-Leu;

(c) the amino acid sequence: IWBAibQGChaRRLGDEINAYYARR (SEQ ID NO: 11) or variant thereof, wherein B is norleucine, and wherein the variant comprises up to 2 amino acids substitutions selected from: B is substituted with M, L, I or V; and R at position 8 of SEQ ID NO: 11 is substituted with Q, D, Aib or Me-Leu; or (d) the amino acid sequence: IWBAibQGH-ChaRRLGDEINAYYARR (SEQ ID NO: 12) or a variant thereof, wherein B is norleucine and H-Cha is homo-cyclohexylalanine, and wherein the variant comprises up to 2 amino acids substitutions selected from: B is substituted with M, L, I or V; and R at position 8 of SEQ ID NO: 12 is substituted with Q, D, Aib or Me-Leu.

10. A method of treating cancer, comprising administering the pharmaceutical composition of claim 5 to a subject expressing myeloid cell leukemia-1 (Mcl-1).

* * * * *